(12) United States Patent
Do et al.

(10) Patent No.: US 12,254,987 B2
(45) Date of Patent: Mar. 18, 2025

(54) ARTIFICIAL INTELLIGENCE FOR IDENTIFYING ONE OR MORE PREDICTIVE BIOMARKERS

(71) Applicant: Certis Oncology Solutions, Inc., San Diego, CA (US)

(72) Inventors: Long Hoang Do, Solana Beach, CA (US); Yuan Hung Chien, San Diego, CA (US); Peter Ellman, San Diego, CA (US)

(73) Assignee: Certis Oncology Solutions, Inc., San Diego, CA (US)

( * ) Notice: Subject to any disclaimer, the term of this patent is extended or adjusted under 35 U.S.C. 154(b) by 0 days.

(21) Appl. No.: 18/125,673

(22) Filed: Mar. 23, 2023

(65) Prior Publication Data

US 2024/0321448 A1    Sep. 26, 2024

(51) Int. Cl.
*G16H 50/20*    (2018.01)
*G16B 25/10*    (2019.01)

(52) U.S. Cl.
CPC ............. *G16H 50/20* (2018.01); *G16B 25/10* (2019.02)

(58) Field of Classification Search
CPC .............................. G16H 50/20; G16B 25/10
See application file for complete search history.

(56) References Cited

U.S. PATENT DOCUMENTS

| | | | | |
|---|---|---|---|---|
| 2015/0240315 A1* | 8/2015 | Blakemore | ............ | A61P 35/00 703/2 |
| 2019/0360052 A1 | 11/2019 | Zhang et al. | | |
| 2020/0115762 A1* | 4/2020 | Khammanivong | .. | C12Q 1/6886 |
| 2020/0365270 A1* | 11/2020 | Kazemi Oskooei | ..... | G06N 3/08 |
| 2021/0363477 A1* | 11/2021 | LeDuc | .................. | C12M 21/08 |
| 2022/0146493 A1* | 5/2022 | Taverna | ................. | G01N 27/12 |
| 2023/0103007 A1* | 3/2023 | Pachter | ................ | A61K 31/506 514/252.16 |

FOREIGN PATENT DOCUMENTS

| WO | 2022087540 A1 | 4/2022 |
|---|---|---|
| WO | 2023165494 A1 | 9/2023 |

OTHER PUBLICATIONS

Sarhadi et al., "Molecular Biomarkers in Cancer", Biomolecules 2022, 12, 1021. https://doi.org/10.3390/biom12081021; 39 pages; Jul. 9, 2021.
Pal et al. Current advances in prognostic and diagnostic biomarkers for solid cancers: Detection techniques and future challenges; https://doi.org/10.1016/j.biopha.2021.112488; Biomedicine & Pharmacotherapy.

(Continued)

*Primary Examiner* — Jay M. Patel
(74) *Attorney, Agent, or Firm* — Procopio, Cory, Hargreaves & Savitch LLP

(57) ABSTRACT

Methods and systems of using at least one hardware processor to train a machine learning algorithm to identify one or more predictive drug molecular features and/or predictive gene biomarkers for cancer treatment is provided. In some embodiments, the method uses at least one cancer drug discovery data set to train at least one learning algorithm in a prediction model, and uses a xenograft mouse model to validate the prediction model, with biological response fed back to the prediction model to further train the learning algorithm.

30 Claims, 5 Drawing Sheets

(56) References Cited

OTHER PUBLICATIONS

Partin, A., et al., Data augmentation and multimodal learning for predicting drug response in patient-derived xenografts from gene expressions and histology images, Frontiers in Medicine, Mar. 7, 2023, 11 pgs, [retrieved May 29, 2023], [online] https://www.frontiersin.org/articles/10.3389/fmed.2023.1058919/full.

Kim, Y., et al., PDXGEM: patient-derived tumor xenograft-based gene expression model for predicting clinical response to anticancer therapy in cancer patients, BMC Bioinformatics, 2020, 21(288), 21 pgs, [retrieved May 29, 2024], [online] https://doi.org/10.1186/s12859-020-03633-z.

Partin, A., Deep learning methods for drug response prediction in cancer: Predominant and emerging trends, Frontiers in Medicine, Feb. 15, 2023, 21 pgs., [retreived May 29, 2024], [online] https://www.frontiersin.org/articles/10.3389/fmed.2023.1086097/full.

International Search report and Written Opinion for PCT App No. PCT/US2024/021374, dated Aug. 7, 2024, 17 pgs.

Bremnes, R.M., et al., The Role of Tumor-Infiltrating Immune Cells and Chronic Inflammation at the Tumor Site on Cancer Development, Progression, and Prognosis, Journal of Thoracic Oncology, 6(4), Apr. 2011, pp. 824-833.

\* cited by examiner

FIG. 3
A. Colon Therapy Prediction Model
B. Lung Therapy Prediction Model
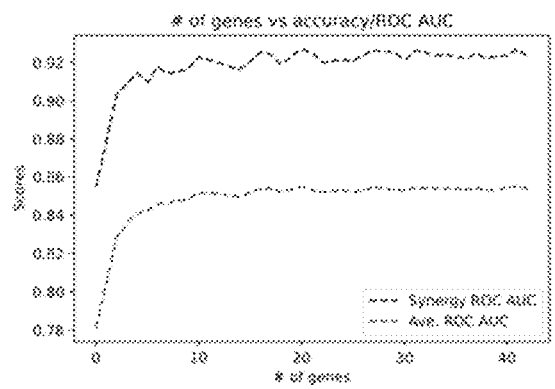
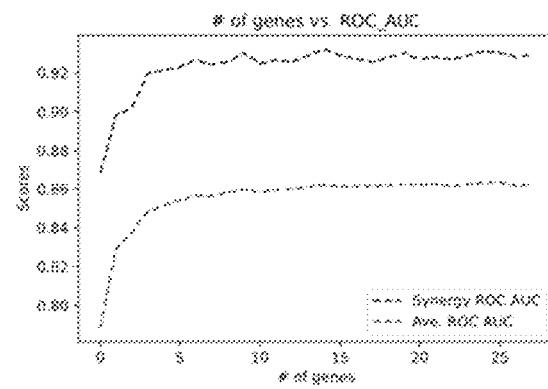
FIG. 4
A. Monotherapy Prediction Model (AUC)
| Cancer Type | $R^2$ | RMSE | Accuracy |
|---|---|---|---|
| Lung | 0.642 | 0.0912 | 0.909 |
| Colorectal | 0.6 | 0.0892 | 0.911 |
| Brain | 0.675 | 0.0948 | 0.905 |
| Breast | 0.650 | 0.0948 | 0.905 |
| Ovary | 0.655 | 0.0911 | 0.909 |
| Skin | 0.693 | 0.0976 | 0.902 |
| Pancreas | 0.586 | 0.1018 | 0.897 |
| Sarcoma | 0.709 | 0.0948 | 0.904 |
B. Monotherapy + Combination (Z-Score)
| Cancer Type | $R^2$ | RMSE | Accuracy |
|---|---|---|---|
| Lung | 0.609 | 0.696 | 0.863 |
| Colorectal | 0.557 | 0.682 | 0.838 |
| Breast | 0.535 | 0.67 | 0.786 |
| Brain | 0.579 | 0.705 | 0.842 |
| Ovary | 0.565 | 0.677 | 0.822 |

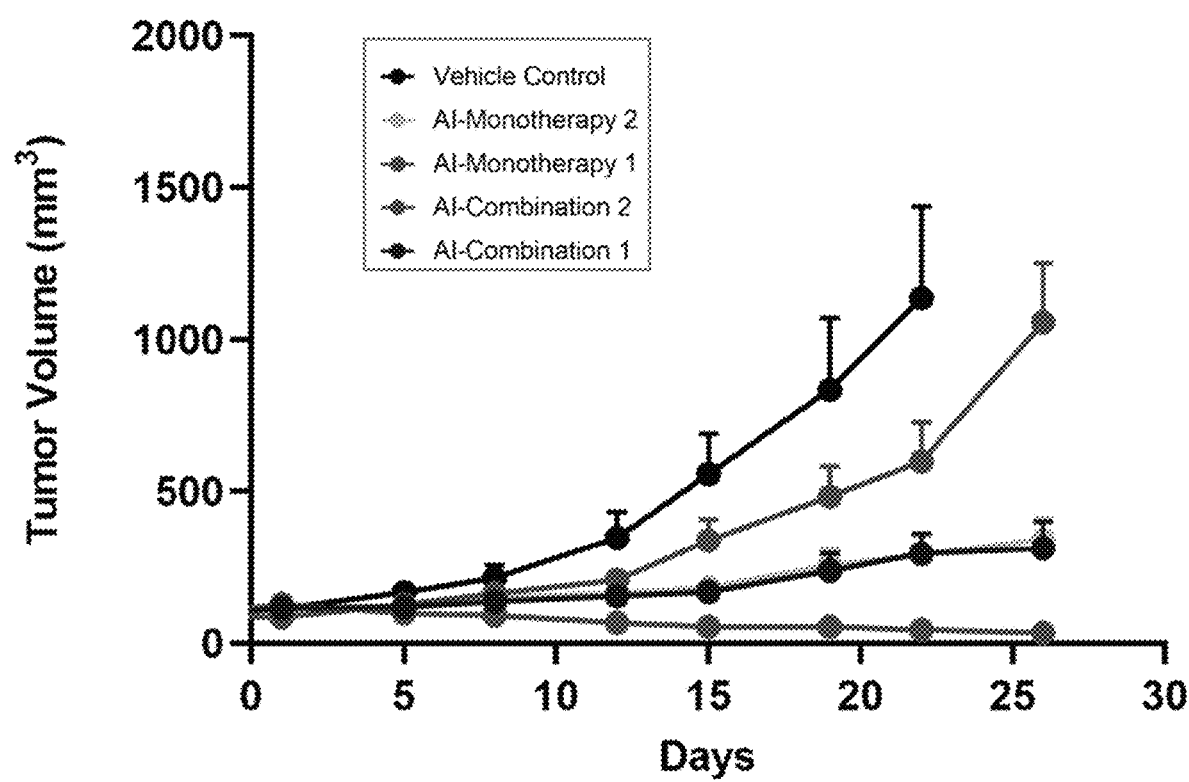

ARTIFICIAL INTELLIGENCE FOR IDENTIFYING ONE OR MORE PREDICTIVE BIOMARKERS

BACKGROUND

The present disclosure relates to systems, software and methods for identifying predictive biomarkers, especially predictive biomarkers for cancer therapeutic response.

SUMMARY OF DISCLOSURE

According to one aspect of the present disclosure, a method of using at least one hardware processor to train an artificial intelligence to identify one or more predictive biomarkers for cancer treatment is provided.

In some embodiments, the method comprises: using at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and validating the prediction model by using a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model to further train the learning algorithm.

In some embodiments of the disclosed method, the human cancer tissue exhibiting the specific set of cancer biomarkers is orthotopically implanted into the multiple immune-deficient mice.

In some embodiments of the disclosed method, the at least one cancer drug discovery data set comprises cancer classification data, cancer biomarker data, drug or drug combination data, and biological response data.

In some embodiments of the disclosed method, for each cancer class, the at least one learning algorithm qualifies drugs or drug combinations in terms of their biological response.

In some embodiments of the disclosed method, for each drug or drug combination under the cancer class, the at least one learning algorithm qualifies cancer biomarkers in terms of their correspondence to the drug's or drug combination's biological response.

In some embodiments of the disclosed method, the cancer classification data comprises cancer cell line information from in vitro screening, patient information from clinical studies, or combination thereof. In some embodiments, the cancer cell line information comprises information selected from the group consisting of cancer cell line identification, TCGA classification, tissue type, tissue sub-type, or combinations thereof.

In some embodiments of the disclosed method, the patient information comprises information selected from cancer type, patient tumor biomarkers, patient age, patient gender, patient weight; patient family history, patient preexisting condition, and combinations thereof.

In some embodiments of the disclosed method, the cancer biomarker data comprises gene expression data. In some embodiment, the gene expression data are normalized using transcripts per million (TPM). In some embodiments, the gene expression data are normalized against the geometric mean of 4 housekeeping genes with low variance.

In some embodiments of the disclosed method, the cancer biomarker data comprises gene methylation data. In some embodiments, the cancer biomarker data comprises protein biomarker data.

In some embodiments of the disclosed method, the drug or drug combination data comprises chemical structures of drugs. In some embodiments, the drug or drug combination data comprises sub-structural features of drugs. In some embodiments, the sub-structural features of drugs comprise descriptor from SMILES specification of the drugs.

In some embodiments of the disclosed method, the biological response data comprises in vitro drug screening results. In some embodiments, the in vitro drug screening results are in the form of IC50 (half maximal inhibitory concentration), AUC (area under the drug response curve), or combination thereof. In some embodiments, the IC50, AUC, or combination thereof is transformed into a normal distribution, and a normalized score is reported as either a standardized z-score or standardized and then scaled from 0 to 1 or from 0 to 100%.

In some embodiments of the disclosed method, the biological response data comprises in vitro drug combination screening results. In some embodiments, the in vitro drug combination screening results are in the form of synergy score obtained through a Highest single agent (HSA) model, Loewe additivity model, Bliss independence model, or zero interaction potency (ZIP) model. In some embodiments, the in vitro drug combination screening results are in the form of Loewe, HSA, Bliss, or ZIP synergy score. In some embodiments, the in vitro drug combination Loewe, HSA, Bliss, or ZIP synergy score is reported as either a standardized z-score or standardized and then scaled from 0 to 1 or from 0% to 100%.

In some embodiments of the disclosed method, the biological response data comprises clinical study results. In some embodiments, the clinical study results comprise safety evaluation, efficacy evaluation, dose response evaluation, pharmacodynamic evaluation, pharmacokinetic evaluation, progression-free survival evaluation, or combinations thereof. In some embodiments, the efficacy evaluation comprises tumor size measurement, tumor burden evaluation, efficacy biomarker evaluation, response evaluation, survival evaluation, or combinations thereof. In some embodiments, the response evaluation, survival evaluation, or combinations thereof is transformed and reported as a scaled efficacy score from 0 to 1 or from 0% to 100%.

In some embodiments of the disclosed method, the biological response data is comprised of xenograft drug monotherapy or drug combination pharmacology results. In some embodiments, the xenograft pharmacology results comprise of tumor size measurement, tumor growth inhibition (TGI), AUC, or combinations thereof. In some embodiments, the TGI or AUC is transformed into a normal distribution and is reported as a standardized z-score or scaled score from 0 to 1 or from 0% to 100%.

In some embodiments of the disclosed method, the at least one cancer drug discovery dataset comprise data from the Genomics of Drug Sensitivity in Cancer (GDSC).

In some embodiments of the disclosed method, the at least one cancer drug discovery dataset comprise data from Drugcomb.org.

In some embodiments of the disclosed method, the at least one cancer drug discovery dataset comprise data from NCI-ALMANAC.

In some embodiments of the disclosed method, the at least one cancer drug discovery dataset comprise data from Cancer Genome Atlas Program.

In some embodiments of the disclosed method, the at least one cancer drug discovery dataset comprise data from Genotype Tissue Expression Project (GTEx).

In some embodiments of the disclosed method, the at least one learning algorithm comprises a supervised learning algorithm. In some embodiments, the at least one learning algorithm comprises an unsupervised learning algorithm.

In some embodiments of the disclosed method, the at least one learning algorithm comprises a regression algorithm, preferably a random-forest regressor.

In some embodiments of the disclosed method, the at least one learning algorithm comprises a classification algorithm, preferably a random-forest classifier, an SVM classifier, or both.

In some embodiments of the disclosed method, the at least one learning algorithm comprises a feature selection algorithm, preferably a Boruta algorithm.

In some embodiments, the disclosed method further comprises applying a dimension reduction algorithm, preferably UMAP, PCA, or both, in the predictive model.

In some embodiments, the disclosed method further comprises independently re-sampling data elements in each data set.

According to another aspect of the present disclosure, a system is provided as comprising: an input unit capable of downloading at least one cancer drug discovery data set; and a training unit capable of using at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and wherein the training unit is capable of further training the learning algorithm by using data obtained from a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with measurement of biological response to the treatment used as new training data for the prediction model.

In some embodiments of the disclosed system, the human cancer tissue exhibiting the specific set of cancer biomarkers is orthotopically implanted into the multiple immune-deficient mice.

In some embodiments of the disclosed system, the at least one cancer drug discovery data set comprises cancer classification data, cancer biomarker data, drug or drug combination data, and biological response data.

In some embodiments of the disclosed system, for each cancer class, the at least one learning algorithm qualifies drugs or drug combinations in terms of their biological response.

In some embodiments of the disclosed system, for each drug or drug combination under the cancer class, the at least one learning algorithm qualifies cancer biomarkers in terms of their correspondence to the drug's or drug combination's biological response.

In some embodiments of the disclosed system, the cancer classification data comprises cancer cell line information from in vitro screening, patient information from clinical studies, or combination thereof. In some embodiments, the cancer cell line information from comprises information selected from the group consisting of cancer cell line identification, TCGA classification, tissue type, tissue sub-type, or combinations thereof.

In some embodiments of the disclosed system, the patient information comprises information selected from cancer type, patient age, patient gender, patient weight; patient family history, patient pre-existing condition, and combinations thereof.

In some embodiments of the disclosed system, the cancer biomarker data comprises gene expression data. In some embodiment, the gene expression data are normalized using transcripts per million (TPM). In some embodiments, the gene expression data are normalized against the geometric mean of 4 housekeeping genes with low variance.

In some embodiments of the disclosed system, the cancer biomarker data comprises gene methylation data. In some embodiments, the cancer biomarker data comprises protein biomarker data.

In some embodiments of the disclosed system, the drug or drug combination data comprises chemical structures of drugs. In some embodiments, the drug or drug combination data comprises sub-structural features of drugs. In some embodiments, the sub-structural features of drugs comprise descriptor from SMILES specification of the drugs.

In some embodiments of the disclosed system, the biological response data comprises in vitro drug screening results. In some embodiments, the in vitro drug screening results are in the form of IC50 (half maximal inhibitory concentration), AUC (area under the drug response curve), or combination thereof. In some embodiments, the IC50, AUC, or combination thereof is transformed into a normal distribution, and a normalized score is reported as either a standardized z-score or standardized and then scaled from 0 to 1 or from 0 to 100%.

In some embodiments of the disclosed system, the biological response data comprises in vitro drug combination screening results. In some embodiments, the in vitro drug combination screening results are in the form of synergy score obtained through a Highest single agent (HSA) model, Loewe additivity model, Bliss independence model, or zero interaction potency (ZIP) model. In some embodiments, the in vitro drug combination screening results are in the form of Loewe synergy score, HSA score, Bliss score, or ZIP score. In some embodiments, the in vitro drug combination Loewe, HSA, Bliss, or ZIP synergy score is reported as either a standardized z-score or standardized and then scaled from 0 to 1 or from 0% to 100%.

In some embodiments of the disclosed system, the biological response data comprises clinical study results. In some embodiments, the clinical study results comprise safety evaluation, efficacy evaluation, dose response evaluation, pharmacodynamic evaluation, pharmacokinetic evaluation, progression-free survival evaluation, or combinations thereof. In some embodiments, the efficacy evaluation comprises tumor size measurement, tumor burden evaluation, efficacy biomarker evaluation, response evaluation, survival evaluation, or combinations thereof. In some embodiments, the response evaluation, survival evaluation, or combinations thereof is transformed and reported as a scaled efficacy score from 0 to 1 or from 0% to 100%.

In some embodiments of the disclosed system, the biological response data is comprised of xenograft drug monotherapy or drug combination pharmacology results. In some embodiments, the xenograft pharmacology results comprise of tumor size measurement, tumor growth inhibition (TGI), AUC, or combinations thereof. In some embodiments, the TGI or AUC is transformed into a normal distribution and is reported as a standardized z-score or scaled score from 0 to 1 or from 0% to 100%.

In some embodiments of the disclosed system, the at least one cancer drug discovery data set comprise data from Genomics of Drug Sensitivity in Cancer (GDSC).

In some embodiments of the disclosed system, the at least one cancer drug discovery data set comprise data from Drugcomb.org.

In some embodiments of the disclosed system, the at least one cancer drug discovery data set comprise data from the Cancer Genome Atlas Program (TCGA).

In some embodiments of the disclosed system, the at least one cancer drug discovery data set comprise data from the Genotype Tissue Expression Project (GTEx).

In some embodiments of the disclosed system, the at least one learning algorithm comprises a supervised learning algorithm. In some embodiments, at least one learning algorithm comprises an unsupervised learning algorithm.

In some embodiments of the disclosed system, the at least one learning algorithm comprises a regression algorithm, preferably a random-forest regressor.

In some embodiments of the disclosed system, the at least one learning algorithm comprises a classification algorithm, preferably a random-forest classifier, an SVM classifier, or both.

In some embodiments of the disclosed system, the at least one learning algorithm comprises a feature selection algorithm, preferably a Boruta algorithm.

In some embodiments, the disclosed system further comprises a dimension reduction algorithm, preferably UMAP, PCA, or both.

In some embodiments, the disclosed system further comprises independently re-sampling data elements in each data set.

According to another aspect of the present disclosure, a non-transitory computer-readable medium having instructions stored therein is provided. The instructions, when executed by a processor, cause the processor to: use at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and train the prediction model by using a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model to further train the learning algorithm.

In some embodiments of the disclosed computer readable medium, the human cancer tissue exhibiting the specific set of cancer biomarkers is orthotopically implanted into the multiple immune-deficient mice.

In some embodiments of the disclosed computer readable medium, the at least one cancer drug discovery data set comprises cancer classification data, cancer biomarker data, drug or drug combination data, and biological response data.

In some embodiments of the disclosed computer readable medium, for each cancer class, the at least one learning algorithm qualifies drugs or drug combinations in terms of their biological response.

In some embodiments of the disclosed computer readable medium, for each drug or drug combination under the cancer class, the at least one learning algorithm qualifies cancer biomarkers in terms of their correspondence to the drug's or drug combination's biological response.

In some embodiments of the disclosed computer readable medium, the cancer classification data comprises cancer cell line information from in vitro screening, patient information from clinical studies, or combination thereof. In some embodiments, the cancer cell line information comprises information selected from the group consisting of cancer cell line identification, TCGA classification, tissue type, tissue sub-type, or combinations thereof.

In some embodiments of the disclosed computer readable medium, the patient information comprises information selected from cancer type, patient age, patient gender, patient weight, patient family history, patient preexisting condition, and combinations thereof.

In some embodiments of the disclosed computer readable medium, the cancer biomarker data comprises gene expression data. In some embodiment, the gene expression data are normalized using transcripts per million (TPM). In some embodiments, the gene expression data are normalized against the geometric mean of 4 housekeeping genes with low variance.

In some embodiments of the disclosed computer readable medium, the cancer biomarker data comprises gene methylation data. In some embodiments, the cancer biomarker data comprises protein biomarker data.

In some embodiments of the disclosed computer readable medium, the drug or drug combination data comprises chemical structures of drugs. In some embodiments, the drug or drug combination data comprises sub-structural features of drugs. In some embodiments, the sub-structural features of drugs comprise descriptor from SMILES specification of the drugs.

In some embodiments of the disclosed computer readable medium, the biological response data comprises in vitro drug screening results. In some embodiments, the in vitro drug screening results are in the form of IC50 (half maximal inhibitory concentration), AUC (area under the drug response curve), or combination thereof. In some embodiments, the IC50, AUC, or combination thereof is transformed into a normal distribution, and a normalized score is reported as either a standardized z-score or standardized and then scaled from 0 to 1 or from 0 to 100%.

In some embodiments of the disclosed computer readable medium, the biological response data comprises in vitro drug combination screening results. In some embodiments, the in vitro drug combination screening results are in the form of synergy score obtained through a Highest single agent (HSA) model, Loewe additivity model, Bliss independence model, or zero interaction potency (ZIP) model. In some embodiments, the in vitro drug combination screening results are in the form of Loewe, HSA, Bliss, or ZIP synergy score. In some embodiments, the in vitro drug combination Loewe, HSA, Bliss, or ZIP synergy score is reported as either a standardized z-score or standardized and then scaled from 0 to 1 or from 0% to 100%.

In some embodiments of the disclosed computer readable medium, the biological response data comprises clinical study results. In some embodiments, the clinical study results comprise safety evaluation, efficacy evaluation, dose response evaluation, pharmacodynamic evaluation, pharmacokinetic evaluation, progression-free survival evaluation, or combinations thereof. In some embodiments, the efficacy evaluation comprises tumor size measurement, tumor burden evaluation, efficacy biomarker evaluation, or combinations thereof. In some embodiments, the response evaluation, survival evaluation, or combinations thereof is transformed and reported as a scaled efficacy score from 0 to 1 or from 0% to 100%.

In some embodiments of the disclosed computer readable medium, the biological response data is comprised of xenograft drug monotherapy or drug combination pharmacology results. In some embodiments, the xenograft pharmacology results comprise of tumor size measurement, tumor growth inhibition (TGI), AUC, or combinations thereof. In some embodiments, the TGI or AUC is transformed into a normal distribution and is reported as a standardized z-score or scaled score from 0 to 1 or from 00% to 100%.

In some embodiments of the disclosed computer readable medium, the at least one cancer drug discovery data set comprise data from the Genomics of Drug Sensitivity in Cancer (GDSC).

In some embodiments of the disclosed computer readable medium, the at least one cancer drug discovery data set comprise data from Drugcomb.org.

In some embodiments of the disclosed computer readable medium, the at least one cancer drug discovery data set comprise data from NCI-ALMANAC.

In some embodiments of the disclosed computer readable medium, the at least one cancer drug discovery data set comprise data from the Cancer Genome Atlas Program (TCGA).

In some embodiments of the disclosed computer readable medium, the at least one cancer drug discovery data set comprise data from the Genotype Tissue Expression Project (GTEx).

In some embodiments of the disclosed computer readable medium, the at least one cancer drug discovery data set comprise data from Genotype Tissue Expression Project (GTEx).

In some embodiments of the disclosed computer readable medium, the at least one learning algorithm comprises a supervised learning algorithm. In some embodiments, the at least one learning algorithm comprises an unsupervised learning algorithm.

In some embodiments of the disclosed computer readable medium, the at least one learning algorithm comprises a regression algorithm, preferably a random-forest regressor.

In some embodiments of the disclosed computer readable medium, the at least one learning algorithm comprises a classification algorithm, preferably a random-forest classifier, an SVM classifier, or both.

In some embodiments of the disclosed computer readable medium, the at least one learning algorithm comprises a feature selection algorithm, preferably a Boruta algorithm.

In some embodiments, the disclosed computer readable medium further comprises a dimension reduction algorithm, preferably UMAP, PCA, or both.

In some embodiments, the disclosed computer readable medium further comprises independently re-sampling data elements in each data set.

DESCRIPTION OF THE FIGURES

The objects and features of the invention can be better understood with reference to the following detailed description and accompanying drawings.

FIG. 3 details the results of feature optimization where only 5-10 genes are shown to be necessary to reach peak optimal prediction accuracy in A) a colon cancer therapy prediction model and B) a lung cancer therapy prediction model.

FIG. 4 details the accuracy results of our in-vitro therapy prediction models for A) prediction models for monotherapies and B) prediction models with both monotherapies and combination therapies combined.

FIG. 6 is an overview of a PDX model validation pharmacology experiment where we show drug response of a triple negative breast cancer orthotopic PDX model to 4 predicted AI therapies.

DETAILED DESCRIPTION

Figure 1:
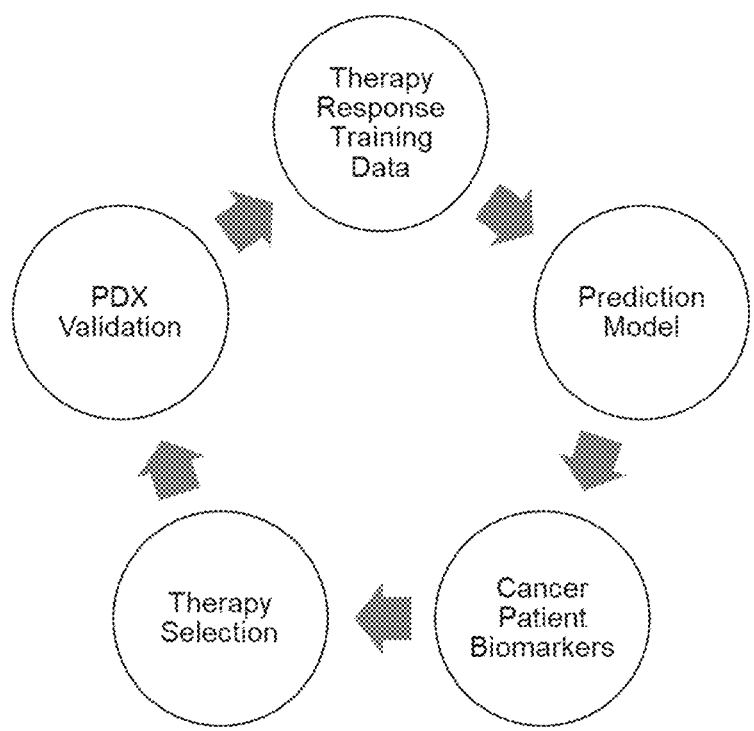
FIG. 1 is a schematic overview of the method, system, and non-transitory computer readable medium according to the present disclosure for building software to identify and validate predictive chemical molecular features and gene biomarkers for cancer treatment.

The present disclosure provides a method, system and software to identify and validate predictive biomarkers which are predictive of human response to a cancer treatment.

Genomic and proteome analysis supplies a wealth of information regarding the numbers and forms of proteins expressed in a cell and provides the potential to identify for each cell, a profile of expressed proteins characteristic of a particular cell state. In some cases, this cell state may be characteristic of an abnormal physiological response associated with a disease. Consequently, identifying and comparing a cell state from a patient with a disease to that of a corresponding cell from a normal patient can provide opportunities to diagnose and control treatment of disease.

Recent advances in transcriptional and proteomic profiling technology have made it possible to apply computational methods to detect changes in expression patterns and their association to disease conditions, thereby facilitating the identification of markers that may contribute to multi-marker combinations with highly accurate diagnostic performance.

While high throughput screening methods provide large data sets of gene expression information, the challenge of bioinformatics remains to develop robust methods for organizing the data into patterns that are reproducibly diagnostic for diverse populations of individuals. The commonly accepted approach has been to pool data from multiple sources to form a combined data set and then to divide the data set into a discovery/training set and a test/validation set. However, both transcription profiling data and protein expression profiling data are often characterized by a large number of variables relative to the available number of samples.

Observed differences between expression profiles of specimens from groups of patients or controls are typically overshadowed by (1) biological variability or unknown sub-phenotypes within the disease or control populations; (2) site-specific biases due to difference in study protocols, specimens handling, etc.; (3) biases due to differences in instrument conditions (e.g., chip batches); and/or (4) variations due to measurement error. False discovery of drug targets remains a serious issue, especially considering the cost and effort typically required for "post-discovery" work such as protein/gene identification and further validation for potential biomarkers.

The present disclosure recognizes that sometimes systematic biases due to site-specific factors can only be detected through careful analysis and comparison of data from multiple sources. The disclosure provides systems, software and methods for analyzing expression profiling data from multiple sources (e.g., such as clinical trial sites) to overcome the possible systematic biases in expression data typically generated in such analyses, thereby reducing the probability of false discovery of drug targets. In one preferred aspect, the invention combines the use bioinformatics and expression profiling of specimens from multiple sources to screen for, identify, and validate biomarkers for a particular biological state or condition of interest. The measurement of these markers in patient samples can provide information that may be the presence, absence or severity of a condition or characteristic of a patient such as a human being. In one aspect, the condition or characteristic is the presence, predisposition or risk of recurrence of a disease.

In some embodiments, the present disclosure provides bioinformatics tools to analyze expression profiling data of samples from two or more independent sources in a way which reduces the sources of variability and biases which result in identification of false targets during the drug discovery process. In some embodiments of the present disclosure, data from multiple sources are not pooled together into a combined data set and then divided into a discovery/training set and a test/validation set. In some embodiments, data from multiple sources (e.g., such as multiple different clinical trial sites) are analyzed separately and independently from the others.

For each source, sufficient sample size and statistical re-sampling methods (e.g., such as bootstrap analysis) help to discover biomarkers that perform well in a representative population and perform consistently well among different randomly selected subpopulations. The use of a re-sampling procedure reduces the compound impact of biological variability and large number of variables in gene expression profiling data.

In some embodiments, the present disclosure involves developing at least two different learning sets (discovery data sets) that have been developed independently of each other. Each learning set includes subject data (data points) from a plurality of subjects. The subject data from each subject indicates a phenotype (form of a biological state class or pathology status) to which the subject belongs, and each subject is classified into one of a plurality of different pathology classes. The different phenotypes generally are pathology related, for example, diseased v. normal, different disease stages, etc. However, they can include any measurable biological characteristic. Each learning set has subject data from at least two subjects belonging to each of the phenotypes. The subject data from each subject comprises measurements of a plurality of data elements from each subject sample.

In some embodiments, the results from the separately and independently conducted analyses are then cross-compared to identify a subset of potential biomarkers that share a comparable level of performance on data from each individual source AND share the same up/down regulation patterns between the different groups of samples across the multiple sources of data.

Biomarkers selected from the cross-comparison are then used to develop a multivariate classification model that classifies a sample (e.g. a patient's cancerous tissue) into one of the biological state classes or conditions. This subset of potential biomarkers, preferably, will be further validated using another independent validation data set. Furthermore, the identities of these potential biomarkers, preferably, will be identified and their performance validated using additional samples and with additional methods (e.g., including, but not limited to immunoassays).

In one preferred aspect, the expression profiling data evaluated is proteomic profiling data (i.e., data relating to the expression of proteins and their modified and processed forms). For example, the method is particularly amenable for use with mass spectrometry-based analysis of a proteome. Therefore, in one aspect, the AI method disclosed herein is used to screen for, identify, and validate predictive biomarkers for cancer treatment. Data (e.g., types of biomarkers expressed, level of expression for each biomarker) from independent data sets are cross-compared to identify those markers predictive of one or more characteristics of the data sets. Such characteristics can include the presence of a condition shared by members of the data sets, such as the presence of a disease.

The expression profile (e.g., presence, absence, quantity) of the biomarkers in a sample (e.g. a patient's cancerous tissue) can be used to identify the status of cell, a tissue, organ, and/or patient. In certain aspects, the expression profile of a single biomarker is indicative of the status. In other aspects, the expression profile of a plurality of markers is indicative of the status.

Definitions

As used herein, the following terms have the meanings ascribed to them unless specified otherwise.

As used in the specification and claims, the singular form "a", "an" and "the" include plural references unless the context clearly dictates otherwise. For example, the term "a cell" includes a plurality of cells, including mixtures thereof. The term "a protein" includes a plurality of proteins.

Also, as used in the description herein and throughout the claims that follow, the meaning of "in" includes "in" and "on" unless the context clearly dictates otherwise.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

A "biomarker" in the context of the present invention refers to a biomolecule, e.g., a protein or a modified, cleaved or fragmented form thereof, a nucleic acid, carbohydrate, metabolite; intermediate, etc. which is differentially present in a sample and whose presence, absence or quantity is indicative of the status of the source of the sample (e.g., cell(s), tissue(s), a patient). The term "biomarker" is used interchangeably with the term "marker."

"Data set" refers to a set of data whose elements are data points.

"Data point" refers to an element of a data set, e.g., a subject sample, identified for example, by a label or patient number identifying the source of the sample.

"Biological state class" refers to a biological characteristic into which a data point can be classed. Each data set comprising data points 1 through i, will have at least two data points representing one of at least two forms of a biological state class—present in the sample source providing the data point (class +1) or absent in the sample source providing the data point (class −1). In one aspect, the class −1 data point represents a control (e.g., negative for a disease), though this is not necessarily so. For example, in certain aspects, the class +1 sample represents a certain stage of a disease (e.g., malignant cancer) while class −1 represents another stage of the disease (e.g., benign cells). What the state class represents will be governed by the nature of the diagnostic test the biomarkers are being selected for. Examples of biological state classes are pathology (pathological v. non-pathological (e.g., cancer v. non-cancer)), drug response (drug responder v. drug non-responder), toxic response (toxic response v. non-toxic response), prognosis (progressor to disease state v. non-progressor to disease state), and, most generally, phenotype (phenotypic condition present v. phenotypic condition absent).

"Data element" refers to features of a data point representing characteristics of the data point. For example, in one aspect, data elements represent expression values of a plurality of different genes in a sample. In another aspect, data elements represent peaks detected by mass spectrometry. In another aspect, data elements represent a variety of phenotypic characteristics, e.g., levels of any biologically significant analyte (e.g., clinical chemistry or hematology laboratory panels), responses to questions in an evaluation test, elements of a medical history, etc.

"Data element value" refers to a value assigned to a data element. The value may be qualitative or quantitative, for example "present or absent," "high, medium or low," or a measured numerical amount.

"Qualifying" a data element refers to assigning a value to the data element to which a selection criterion can be applied.

"Selection criteria" refers to a criterion or criteria established by a user implementing the method applied to a qualifier to select a data element into an initial subset. The selection criteria may be a cut-off for a numerical qualifier or a class for a qualitative qualifier. Examples of cut-off criteria are "data elements in the top ten percent of discriminatory power" or "data elements providing at least 80% specificity and at least about 70% sensitivity." Examples of class criteria are "good" or "bad" data elements based on the qualifier; to some extent this will depend on the nature of the biological state class of interest as for a disease with few diagnostic markers data elements with lower specificity or sensitivity may be selected with a lower numerical or qualitative qualifier. The selection criteria may initially be that the data element is consistently better than other data elements in the plurality of data points in the data set in identifying the biological state class.

As used herein, the term "correspond/correspondence to" refers to the ability of a system or component of a system to receive input data from another system or component of a system and to provide an output response in response to the input data. "Output" may be in the form of data or may be in the form of an action taken by the system or component of the system.

As used herein, "gene expression level" or "expression level of a gene" refers to the nature and amount of a molecule encoded by the gene, e.g., an RNA or polypeptide. The expression level of an mRNA molecule is intended to include the amount of mRNA, which is determined by the transcriptional activity of the gene encoding the mRNA, and the stability of the mRNA, which is determined by the half-life of the mRNA. The gene expression level is also intended to include the amount of a polypeptide corresponding to a given amino acid sequence encoded by a gene. Accordingly, the expression level of a gene can correspond to the amount of mRNA transcribed from the gene, the amount of polypeptide encoded by the gene, or both. Expression levels of a gene product may be further categorized by expression levels of different forms of gene products. For example, RNA molecules encoded by a gene may include differentially expressed splice variants, transcripts having different start or stop sites, and/or other differentially processed forms. Polypeptides encoded by a gene may encompass cleaved and/or modified forms of polypeptides. Further, multiple forms of a polypeptide having a given type of modification can exist. For example, a polypeptide may be phosphorylated at multiple sites and express different levels of differentially phosphorylated proteins.

As used herein, a "gene expression profile" refers to a characteristic representation of a gene's expression level in a specimen such as a cell or tissue. The determination of a gene expression profile in a specimen from an individual is representative of the gene expression state of the individual. A gene expression profile reflects the expression of messenger RNA or polypeptide or a form thereof encoded by one or more genes in a cell or tissue. An "expression profile" refers more generally to a profile of biomolecules (nucleic acids, proteins, carbohydrates) which shows different expression patterns among different cells or tissue. The term "expression profile" encompasses the term "gene expression profile".

As used herein, a "computer program product" refers to the expression of an organized set of instructions in the form of natural or programming language statements that is contained on a physical media of any nature (e.g., written, electronic, magnetic, optical or otherwise) and that may be used with a computer or other automated data processing system of any nature (but preferably based on digital technology). Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in preselected ways may be provided in a number of forms, including, but not limited to, original source code, assembly code, object code, machine language, encrypted or compressed versions of the foregoing and any and all equivalents.

Cancer Discovery Data Sets

The present disclosure provides a data element selection method that reduces the chances of selecting a classifier whose discriminatory power is biased toward sampling differences rather than differences in forms of biological state classes. In particular, the classifier can be a biomarker such as biological molecules exhibiting variability in expression profiling (transcription profiling, proteome profiling, and the like) and clinical sampling. In one preferred aspect of the invention, biomarkers are obtained from proteomic analysis of patient samples. However, the classifier also can be any other phenotypic trait.

Data sets are likely to include biases or preanalytical variables that produce "false" classifiers/biomarkers—that is, biomarkers that differentiate groups not on the basis of the underlying biological state being studied, but the on the basis of the particular bias. For example, if a data set is sex-biased as to the presence/absence of a disease, then certain highly discriminatory classifiers/biomarkers may be differentiating data points based on sex rather than the disease. Similarly, if diseased and normal samples in a data set are handled differently, then a classifier/biomarker may differentiate data points based on differences in handling rather than disease.

In independent data sets the likelihood of the same biases being present is diminished. Therefore, classifiers/biomarkers that are common to all independent data sets are more likely to discriminate based on the biological state of interest, rather than some experimental bias. Accordingly, two data sets are independent if they are collected in such a way as to significantly decrease the chance of being subject to the same bias, i.e., data sets are independent if the populations used to obtain these data sets show a statistically significant difference with respect to at least one preanalytical variable. The best way to diminish biases between data sets is to collect data points from different sites in different geographical locations. In this way, bias factors are more likely to be randomized between the different data sets and, therefore, eliminated in the intersection subset of likely classifiers/biomarkers.

Additional or alternative ways to diminish bias include collecting data points from at different times and/or or from populations which differ as to one or more of such nonlimiting preanalytical variables such as: gender, age, ethnicity, sample collection parameters, sample processing parameters, weight, diet, medication status, medical condition, amount of physical exercise, pregnancy and menstruation, presence and/or level of circulating antibodies, clinical characteristics (e.g., PSA levels, cholesterol levels, familial history of disease, etc.). Preferably, populations differ as to many preanalytical variables.

In the selection of some types of biomarkers (e.g., biomarkers associated with a specific disease), providing populations which differ as to certain preanalytical variables may be particularly important. For example, in identifying biomarkers for decreased protein C levels, providing populations which differ as to other thrombotic risk factors may be desired.

The present disclosure recognizes that, in some embodiments, identifying characterizing profiles, such as expression profiles of cells having a given cell state, lead to the discovery of classifiers, such as biomarkers, which can be used to identify that cell state with high probability (e.g., having specificity of at least about 80% and sensitivity of at least about 70% in diagnostic tests). The expression profiles can be derived from the expression of nucleic acids (e.g., RNA transcripts, including differentially spliced or processed forms thereof), proteins (including modified and/or processed forms thereof), carbohydrates (e.g., lectins) and the like. In one aspect, the cell state reflects the state of a patient from which the cell was derived and is diagnostic of physiological processes being experienced by the patient (e.g., such as pathological responses experienced when the patient has or is developing, or is recovering from a disease).

As a first step, a plurality of independent data sets is obtained. The data sets comprise data points, e.g., a label referring to a sample number or patient number, representing a plurality of samples from multiple sample sources. Each data set comprises a plurality of forms of at least one biological state class, with a plurality of data points (samples) belonging to each of the forms of the class. For example, a biological state class can include, but is not limited to: presence/absence of a disease in the source of the sample (i.e., a patient from whom the sample is obtained); stage of a disease; risk for a disease; likelihood of recurrence of disease; a shared genotype at one or more genetic loci (e.g., a common HLA haplotype; a mutation in a gene; modification of a gene, such as methylation, etc.); exposure to an agent (e.g., such as a toxic substance or a potentially toxic substance, an environmental pollutant, a candidate drug, etc.) or condition (temperature, pH, etc.); a demographic characteristic (age, gender, weight; family history; history of preexisting conditions, etc.); resistance to a drug, sensitivity to a drug (e.g., responsiveness to a drug) and the like.

Data sets are independent of each other to reduce collection bias in ultimate classifier selection. For example, they can be collected from multiple sources and may be collected at different times and from different locations using different exclusion or inclusion criteria, i.e., the data sets may be relatively heterogeneous when considering characteristics outside of the characteristic defining the biological state class. Factors contributing to heterogeneity include, but are not limited to, biological variability due to sex, age, ethnicity; individual variability due to eating, exercise, sleeping behavior; and sample handling variability due to clinical protocols for blood processing. However, a biological state class may comprise one or more common characteristics (e.g., the sample sources may represent individuals having a disease and the same gender or one or more other common demographic characteristics).

In one aspect, the data sets from multiple sources are generated by collection of samples from the same population of patients at different times and/or under different conditions. However, data sets from multiple sources do not comprise a subset of a larger data set, i.e., data sets from multiple sources are collected independently (e.g., from different sites and/or at different times, and/or under different collection conditions).

In one preferred aspect, a plurality of data sets is obtained from a plurality of different clinical trial sites and each data set comprises a plurality of patient samples obtained at each individual trial site. Sample types include, but are not limited to, blood, serum, plasma, nipple aspirate, urine, tears, saliva, spinal fluid, lymph, cell and/or tissue lysates, laser micro-dissected tissue or cell samples, embedded cells or tissues (e.g., in paraffin blocks or frozen); fresh or archival samples (e.g., from autopsies). A sample can be derived, for example, from cell or tissue cultures in vitro. Alternatively, a sample can be derived from a living organism or from a population of organisms, such as single-celled organisms. Thus, for example, in a method for discovering biomarkers for a particular cancer, blood samples for might be collected from subjects selected by independent groups at two different test sites, thereby providing the samples from which the independent data sets will be developed.

In some embodiments of the disclosed method, the at least one cancer drug discovery data set comprises cancer classification data, cancer biomarker data, drug or drug combination data, and biological response data.

In some embodiments of the disclosed method, for each cancer class, the at least one learning algorithm qualifies drugs or drug combinations in terms of their biological response.

In some embodiments of the disclosed method, for each drug or drug combination under the cancer class, the at least one learning algorithm qualifies cancer biomarkers in terms of their correspondence to the drug's or drug combination's biological response.

In some embodiments of the disclosed method, the cancer classification data comprises cancer cell line information from in vitro screening, patient information from clinical studies, or combination thereof. In some embodiments, the cancer cell line information from comprises information selected from the group consisting of cancer cell line identification, TCGA classification, tissue type, tissue sub-type, or combinations thereof.

In some embodiments of the disclosed method, the patient information comprises information selected from cancer type, patient age, patient gender, patient weight; patient family history, patient preexisting condition, and combinations thereof.

In some embodiments of the disclosed method, the cancer biomarker data comprises gene expression data. In some embodiment, the gene expression data are normalized using transcripts per million (TPM). In some embodiments, the gene expression data are normalized against the geometric mean of 4 housekeeping genes with low variance.

In some embodiments of the disclosed method, the cancer biomarker data comprises gene methylation data. In some embodiments, the cancer biomarker data comprises protein biomarker data.

In some embodiments of the disclosed method, the drug or drug combination data comprises chemical structures of drugs. In some embodiments, the drug or drug combination data comprises sub-structural features of drugs. In some embodiments, the sub-structural features of drugs comprise descriptor from SMILES specification of the drugs.

In some embodiments of the disclosed method, the biological response data comprises in vitro drug screening results. In some embodiments, the in vitro drug screening results are in the form of IC50 (half maximal inhibitory concentration), AUC (area under the drug response curve), or combination thereof.

In some embodiments of the disclosed method, the biological response data comprises in vitro drug combination screening results. In some embodiments, the in vitro drug combination screening results are in the form of synergy score obtained through a Highest single agent (HSA) model, Loewe additivity model, or Bliss independence model. In some embodiments, the in vitro drug combination screening results are in the form of Loewe synergy score.

In some embodiments of the disclosed method, the biological response data comprises clinical study results. In some embodiments, the clinical study results comprise safety evaluation, efficacy evaluation, dose response evaluation, pharmacodynamic evaluation, pharmacokinetic evaluation, progression-free survival evaluation, or combinations thereof. In some embodiments, the efficacy evaluation comprises tumor size measurement, tumor burden evaluation, efficacy biomarker evaluation, or combinations thereof.

In some embodiments of the disclosed method, the at least one cancer drug discovery data set comprise Genomics of Drug Sensitivity in Cancer (GDSC).

In some embodiments of the disclosed method, the at least one cancer drug discovery data set comprise data from Drugcomb.org.

In some embodiments of the disclosed method, the at least one cancer drug discovery data set comprise data from Cancer Genome Atlas Program.

In some embodiments of the disclosed method, the at least one cancer drug discovery data set comprise data from Genotype Tissue Expression Project (GTEx).

In Vitro Cell Line Drug Screening Data Sets

In some embodiments, the present disclosure uses drug compound, drug response, tissue type, and genetic molecular data from large cell line sensitivity screenings, such as CCLE, CTRP, and GDSC. Those data sets include data points with cell line molecular data, cell line drug response data, and cell line tissue type, among others.

Molecular data for CCLE, CTRP, and GDSC data sets was obtained directly from the source dataset. Molecular data included gene expression, copy number information, and mutation information. Expression data comes from next-generation sequencing of RNA (RNAseq) and values are continuous. Copy number information comes from whole exome sequencing and is continuous. Mutation information is derived from whole exome sequencing and is represented by mutation frequency of the gene allele.

Drug information for CCLE, CTRP and GDSC data sets was obtained from the PharmacoGx package or directly from the source database. Chemical structure of drugs were obtained as Simplified Molecular Input Line Entry System (SMILES) from PubChem and converted to drug molecular descriptors using RDKit.

Drug response data included three metrics: IC50, AUC, and viability at 1 µM. IC50 (half maximal inhibitory concentration) and AUC (area under the drug response curve) information was obtained from the PharmacoGx package or directly from the source database (GDSC, CCLE, CTRP).

In Vitro Cell Line Drug Combination Data Sets

In some embodiments, the present disclosure uses molecular information, drug response, tissue type, and genetic molecular data from large drug combination cell line sensitivity screenings, such as NCI-ALMANAC and Drugcombo.org. Those data sets include data points containing cell line molecular data, cell line drug response data, and cell line tissue type, among others.

Molecular data for NCI-ALMANAC and Drugcombo.org data sets was obtained directly from the source dataset or CCLE and GDSC. Molecular data included gene expression, copy number information, and mutation information. Expression data comes from next-generation sequencing of RNA (RNAseq) and values are continuous. Copy number information comes from whole exome sequencing and is continuous. Mutation information is derived from whole exome sequencing and is represented by mutation frequency of the gene allele.

Drug information for NCI-ALMANAC and Drugcombo.org was obtained from the source dataset. Chemical structure of drugs were obtained as Simplified Molecular Input Line Entry System (SMILES) from PubChem and converted to drug molecular descriptors using RDKit.

Combination drug response values for NCI-ALMANAC and Drugcombo.org data sets were obtained directly from the source dataset and include the following metrics: IC50, AUC, and synergy scores. Synergy scores are obtained from a Highest single agent (HSA) model, Loewe additivity model, Bliss independence model, or zero interaction potency (ZIP) model.

Clinical Study Data Sets

In some embodiments, the present disclosure uses molecular information, drug response, tissue type, and genetic molecular data from clinical study data from the Cancer Genome Atlas project (TCGA). Those data sets include data points containing patient molecular data, patient drug response data, patient survival data, and patient cancer type, among others.

Molecular data for TCGA data sets was obtained from the Genomic Data Commons (GDC) data portal. Molecular data included gene expression, copy number information, and mutation information. Expression data comes from next-generation sequencing of RNA (RNAseq) and values are continuous. Copy number information comes from whole exome sequencing and is continuous. Mutation information is derived from whole exome sequencing and is represented by mutation frequency of the gene allele.

Drug information for TCGA was obtained from the GDC data portal. Chemical structure of drugs were obtained as Simplified Molecular Input Line Entry System (SMILES) from PubChem and converted to drug molecular descriptors using RDKit.

Patient drug response for TCGA is defined under the Response Evaluation Criteria In Solid Tumors (RECIST) and Cheson criteria in hematologic cancers. RECIST criteria include the following classifications: complete response (CR), partial response (PR), stable disease (SD), progressive disease (PD), and inevaluable (NE). Cheson criteria include the following classifications: complete response (CR), complete response unconfirmed (CRu), partial response (PR), stable disease (SD), relapsed disease (RD), and progressive disease (PD). Patient survival endpoints in TCGA is measured as continuous value in days.

Learning Algorithm

The present disclosure uses the cancer discovery data sets to train at least one learning algorithm that is used in a prediction model, wherein the trained prediction model is capable of qualifying a plurality of drugs or drug combinations in terms of their predicted biological response to a human cancer tissue exhibiting a specific set of cancer biomarkers.

In some embodiments of the disclosed method, at least one learning algorithm comprises a supervised learning algorithm. In some embodiments, at least one learning algorithm comprises an unsupervised learning algorithm.

In some embodiments of the disclosed method, at least one learning algorithm comprises a multivariate regression algorithm, including random-forest, support vector machines, and artificial neural networks.

In some embodiments of the disclosed method, at least one learning algorithm comprises a classification algorithm, including random-forest, support vector machines, and artificial neural networks.

In some embodiments of the disclosed method, at least one learning algorithm comprises a feature selection algorithm, preferably a Boruta algorithm.

In some embodiments, the disclosed method further comprises a dimension reduction algorithm, preferably UMAP, PCA, or both.

In some embodiments, the disclosed method further comprises independently re-sampling data elements in each data set.

Selecting Initial Subset

A subset of data elements, e.g., genes or proteins, is now selected from each data set based on selection criteria. Generally, the genes or proteins that are the "best" predictors from each data set will be selected. For example, the selection criteria might be to "top ten percent" or "the genes or proteins that provide a specified level of model predicted accuracy." All the data elements from each data set that meet the selection criteria are selected for initial subsets. For example, if there are one hundred genes or proteins that have been ranked in each data set, the top ten percent or top ten genes or proteins each, might be selected for the initial data sets.

Selecting Intersection Subset

Most often, these initial subsets will not be identical in terms of the data elements that populate them. However, if they contain data elements in common, these data elements can be selected into an intersection subset. So, for example the initial subset from data set 1 might contain genes or proteins 1, 3, 5, 7 and 9. The initial subset from data set number 2 might contain genes or proteins 1, 2, 3, 4 and 5. The intersection subset could contain any or all of genes or proteins 1, 3 and 5, as the data elements common to both initial subsets.

More specifically, the results from the plurality of data sets are cross-compared to determine a final set of common data elements with consistent expression patterns as a panel of potential biomarkers. Thus, data elements which are selected or qualified as having good "values" or "weights" using the learning algorithms described above in independent discovery data sets are compared, to select an intersection subset of data elements, wherein the data elements in the intersection subset are those which have good values for a plurality of data sets, i.e., the data elements are consistently good biomarkers. In some cases, a "good value" refers to a data element which has greater than at least 80% specificity and greater than at least about 70% sensitivity in tests to detect or diagnose the biological state class.

Collecting Data Points and Generating Data Elements

Data points representing individual samples within a data set are collected. Each data point comprises data elements. A plurality of data points in the data set is characterized by belonging to the same form of biological state class. For example, each data point which belongs to the same biological state class may represent a sample from a patient identified as having a disease of interest for which biomarkers are being identified.

Data elements are features of a data point representing characteristics of the data point. For example, in one aspect, data elements represent expression values of a plurality of different genes in a sample from a patient having a disease shared in common among patients contributing samples to the data set. Any method for expression profiling known in the art may be used to obtain expression values and is encompassed within the scope of the invention.

Data elements (e.g., gene expression values) can be obtained by transcriptional profiling and/or by proteome profiling. Transcriptional profiling techniques include, but are not limited to: Sequencing by synthesis (SBS), Northern blots, qPCR and RT-PCR-based differential display methods, nuclease protection, representation different analysis (RDA), suppression subtractive hybridization (SSH), and enzymatic degrading subtraction (EDS), gene array profiling, cDNA fingerprinting, subtractive hybridization, serial analysis of gene expression, or SAGE, and the like. Proteome profiling techniques include, but are not limited to: two-hybrid analysis, fluorescence resonance energy transfer (MET), two-dimensional gel electrophoresis, mass spectrometry (e.g., laser desorption/ionization mass spectrometry), fluorescence (e.g. sandwich immunoassay), surface plasmon resonance, ellipsometry and atomic force microscopy.

Other types of biomolecules which are differentially expressed may be profiled to provide data elements. For example, carbohydrates such as lectins (e.g., such as glycans) have diverse expression patterns which can provide data values for data elements comprising a data point.

Preferred methods of expression profiling are high throughput and obtain data elements from greater than about ten, greater than about 50, greater than about 100, greater than about 200, or greater than about 500 samples in data set.

Preferably, data elements are transformed to reduce the number of feature dimensions using algorithms such as UMAP or PCA. For example, 20000 genes can be reduced to only a few hundred dimensions.

Preferably, a data element is represented as a vector of numerical values including a value representing the level of a sample component represented by a data element and at least one other characteristic of the sample component/data element, such as its name or descriptor.

Qualifying Data Elements

In the next step, data elements obtained from an expression profiling method are qualified using any sort of multivariate analysis. In one method qualification involves using a pattern recognition process, such as a classification model.

Classification models can be trained from "known data elements" that are pre-classified (e.g., cancerous or not cancerous, cancer type). The data elements used to form the classification model can be referred to as a "training data set" or "discovery data set". Once trained, the classification model can recognize patterns in data derived from data elements from unknown samples. The classification model can then be used to classify the unknown samples into classes. This can be useful, for example, in predicting whether a particular biological sample is associated with a certain biological condition (e.g., having a disease or not having a disease, and the disease type).

Classification models can be formed using any suitable statistical classification (or "learning") method that attempts to segregate bodies of data into classes based on objective parameters present in the data. Classification methods may be either supervised or unsupervised. Supervised and unsupervised classification processes are known in the art and reviewed in Jain, IEEE Transactions on Pattern Analysis and Machine Intelligence 22 (1): 4-37, 2000, for example. In selecting a classification method, a balance must be reached between reducing the number of data elements to simplify analysis while minimizing risk of losing useful information.

Unsupervised classification attempts to learn classifications based on similarities in the discovery/training data set, without pre-classifying the data elements (e.g., expression data) from which the training data set was derived.

Unsupervised learning methods include cluster analyses. A cluster analysis attempts to divide the data into "clusters" or groups that ideally should have members that are very similar to each other, and very dissimilar to members of other clusters.

In supervised classification, training data containing examples of known categories are presented to a learning mechanism, which learns one or more sets of relationships that define each of the known classes using a learning algorithm. New data may then be applied to the learning mechanism, which then classifies the new data using the learned relationships. Differentially expressed sample components (i.e., defining data elements of a data point) may be identified by using a set of data elements whose values represent the expression of the sample components as training data in which the identity (i.e., label corresponding to a sample number/patient number) of each data point is known beforehand. A supervised learning technique derives a classification model (classifier) that assigns data elements obtained from a plurality of data points to a predefined number of known classes with minimum error. The contributions of individual variables to the classification model are then analyzed as a measurement of the value of the data elements, i.e., which data elements are likely to serve as biomarkers with good discriminatory power (i.e., the ability of the biomarker to discriminate between data points which have a biological state from those which do not). Each common data element in each data point, independently for each data set, is qualified based on the ability of the data element to classify a data point into a biological state class, as a function of data element value.

There are different approaches to the derivation of classification models and generally the type of classification approach used is not a limiting feature of the invention.

The present disclosure in some embodiments integrates a re-sampling procedure into the evaluation of expression data to decrease the impact of variation among samples within a data set (e.g., samples from patients from a clinical trial site) and among different data sets (e.g., samples from patients from different clinical trial sites using different exclusion and inclusion criteria and sampling populations with different demographic characteristics). Re-sampling methods such as bootstrapping, bagging, boosting, Monte Carlo simulations, and the like, are applied, preferably in supervised learning contexts, e.g., using the learning algorithms disclosed herein.

Accordingly, in one aspect, multiple data sets are independently repeatedly divided into subsets comprising test data points (class +1 data points) and compared to reference or control data points (class −1 data points).

In each re-sampling run, data element(s) are selected that contribute significantly and consistently to the separation of data points having the at least one common characteristic from those which do not, i.e., to identify biomarkers which are diagnostic of the at least one common characteristic. Parameters such as mean, variance and confidence intervals of sampled data elements (e.g., confidence scores for expression data) are measured to determine the distribution of the parameters and to identify, outlier scores to form a short list of candidate biomarkers represented by the data elements. For example, expression values (such as sequenced read counts) with high mean ranks and small standard deviations may be selected to for this list. By performing such analyses independently for each of a plurality of data sets, the possibility of choosing data elements as a result of biases or artifacts in data is reduced, thereby reducing the possibility of false discovery of biomarkers.

By this method, data elements are identified with high confidence values (a selected difference from a null (randomized) distribution being accepted as statistically significant with minimal false discovery, e.g., $FDR \leq 0.05$) and which are expressed qualitatively in the same manner (over-expressed or under-expressed in both data sets). Outliers of high confidence are ranked from those showing the greatest difference in expression between a test data point and a reference data point (i.e., the most diagnostic) to those which show the least amount of difference (i.e., least diagnostic).

Thus, for example, gene expression or protein expression data from a collection of samples may yield expression data on over twenty thousand genes or proteins: Each is a data element and its measured expression level is a data element value. After subjecting a data set to the selected form of analysis, the ability of each gene or protein, based on its expression level, to classify a particular sample (data point) as cancerous or non-cancerous and if cancerous, belonging to which cancer type class (form of biological state class) is determined, or "qualified." Each gene or protein might then be ranked from most discriminating to least discriminating.

Using Learning Algorithm in Predictive Model

The data elements in the intersection subset can be used in multivariate models to generate multivariate regression algorithms. To construct multivariate predictive models, the data from the plurality of data sets are combined and randomly divided into a discovery training set and a test set.

The performance of the panel of potential biomarkers identified from re-sampling and cross-comparison and derived predicted models are evaluated on the test set to identify those biomarkers which survive and which remain highly diagnostic of at least one common characteristic. Predictive models are validated on independent data elements from one or more new data sets sharing at least one common characteristic and which have not been involved in biomarker discovery and the model construction process. Independent validation may be performed on data sets which comprise larger populations of data points or are analyzed using different method (e.g., with a different expression profiling technique from the one used to initially obtain the data elements, such as by an immunoassay), obtaining validation training sets that may be used to identify the most highly discriminatory biomarkers of those being tested. Statistical methods for evaluation of validation data sets include sensitivity and specificity estimation and receiver-operating characteristic (ROC) curve analysis, among others.

The multivariate regression algorithm thus generated can be tested against another independent "validation" data set to determine the ultimate power of the algorithm. The validation data set should be independent of all of the discovery data sets used to discover the biomarkers from which the regression algorithm was generated.

Biomarkers can be evaluated after re-sampling, though more preferably, after cross-comparison, to identify additional features of the biomarkers which can be used to characterize validation data sets. For example, sequence information for a peptide or nucleic acid biomarker may be determined. The additional feature(s) may be used to generate probes to test for the presence of the biomarker in test samples (new data points) in data sets used to validate the biomarker. Additional features may include sequence data regarding a larger sequence of which the biomarker sequence is a subsequence (e.g., sequence data for a gene or protein from which the nucleic acid or peptide was derived). Such data may be obtained by using the biomarker sequence to query a database, such as a gene sequence, protein sequence, or glycomic database. Using this method, the sequences of other markers can be identified if these markers are known in the databases.

Preferably, a data element is identified as a biomarker when it is able to predict with greater than 70%, preferably greater than 80%, and still more preferably, greater than 90% accuracy, the presence or absence of a characteristic of a member of a data set. In certain aspects, a plurality of data elements combined can provide the desired predictive value. In certain aspects, combinations with high predictive value may include data elements with lower confidence and may be more predictive than single data elements with higher confidence values. Combinations of data elements suitable for use as biomarkers may be identified by pairing in an ordered or random approach, for example.

Validation by Xenograft Mouse Model

The predictive model utilizing at least one learning algorithm according to the present disclosure is further validated by using a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model to further train the learning algorithm. In some embodiments of the disclosed method, the human cancer tissue exhibiting the specific set of cancer biomarkers is orthotopically implanted into multiple immune-deficient mice.

Patient derived xenografts (PDX) are models of cancer where the tissue or cells from a human patient's tumor are implanted into an immunodeficient or humanized mouse. PDX models are used to create an environment that allows for the natural growth of cancer, its monitoring, and corresponding treatment evaluations for the original patient as well as patients with similar cancer profiles.

Tumor Xenotransplantation

Several types of immunodeficient mice can be used to establish PDX models:

athymic nude mice, severely compromised immune deficient (SCID) mice, NOD-SCID mice, and recombination-activating gene 2 (Rag2)-knockout mice.[2] The mice used must be immunocompromised to prevent transplant rejection. The NOD-SCID mouse is considered more immunodeficient than the nude mouse, and therefore is more commonly used for PDX models because the NOD-SCID mouse does not produce natural killer cells.

When human tumors are resected, necrotic tissues are removed and the tumor can be mechanically sectioned into smaller fragments, chemically digested, or physically manipulated into a single-cell suspension. There are advantages and disadvantages in utilizing either discrete tumor fragments or single-cell suspensions. Tumor fragments retain cell-cell interactions as well as some tissue architecture of the original tumor, therefore mimicking the tumor microenvironment. Alternatively, a single-cell suspension enables scientists to collect an unbiased sampling of the whole tumor, eliminating spatially segregate subclones that are otherwise inadvertently selected during analysis or tumor passaging. However, single-cell suspensions subject surviving cells to harsh chemical or mechanical forces that may sensitize cells to anoikis, taking a toll on cell viability and engraftment success.

Heterotopic and Orthotopic Implantation

Unlike creating xenograft mouse models using existing cancer cell lines, there are no intermediate in vitro processing steps before implanting tumor fragments into a murine host to create a PDX. The tumor fragments are either implanted heterotopically or orthotopically into an immunodeficient mouse. With heterotopic implantation, the tissue or cells are implanted into an area of the mouse unrelated to the original tumor site, generally subcutaneously or in subrenal capsular sites. The advantages of this method are the direct access for implantation, and ease of monitoring the tumor growth. With orthotopic implantation, scientists transplant the patient's tumor tissue or cells into the corresponding anatomical position in the mouse. Subcutaneous PDX models are unlikely to produce metastasis in mice, nor do they simulate the initial tumor microenvironment, with engraftment rates of 40-60%. Subrenal capsular PDX maintains the original tumor stroma as well as the equivalent host stroma and has an engraftment rate of 95%. Ultimately, it takes about 2 to 4 months for the tumor to engraft varying by tumor type, implant location, and strain of immunodeficient mice utilized; engraftment failure should not be declared until at least 6 months.[2] Researchers may use heterotopic implantation for the initial 0engraftment from the patient to the mouse, then use orthotopic implantation to implant the mouse-grown tumor into further generations of mice.

Generations of Engraftments

The first generation of mice receiving the patient's tumor fragments are commonly denoted F0. When the tumor becomes sufficient in size in the F0 mouse, researchers passage the tumor over to the next generation of mice. Each generation thereafter is denoted F1, F2, F3 . . . Fn. For drug development studies, expansion of mice between the F3 and F10 generation is often utilized to ensure that the PDX has not genetically or histologically diverged from the patient's tumor.[8]

Advantages Over Cancer Cell Lines for Predictive Model Validation

Without wishing to be bound by any particular theory, the present disclosure recognizes one or combinations of several factor that makes PDX mouse models a better validation tool than the cancer cell line screening or cancer cell line-derived xenograft models (CDX). First, cancer cell lines are originally derived from patient tumors, but acquire the ability to proliferate within in vitro cell cultures. As a result of in vitro manipulation, cell lines that have been traditionally used in cancer research undergo genetic transformations that are not restored when cells are allowed to grow in vivo. Because of the cell culturing process, which includes enzymatic environments and centrifugation, cells that are better adapted to survive in culture are selected, tumor resident cells and proteins that interact with cancer cells are eliminated, and the culture becomes phenotypically homogeneous.

Second, when implanted into immunodeficient mice, cell lines do not easily develop tumors and the result of any successfully grown tumor is a genetically divergent tumor unlike the heterogeneous patient tumor. Researchers are beginning to attribute the reason that only 5% of anti-cancer agents are approved by the Food and Drug Administration after pre-clinical testing to the lack of tumor heterogeneity and the absence of the human stromal microenvironment. Specifically, cell line-xenografts often are not predictive of the drug response in the primary tumors because cell lines do not follow pathways of drug resistance or the effects of the microenvironment on drug response found in human primary tumors.

Third, many PDX models have been successfully established for breast, prostate, colorectal, lung, and many other cancers because there are distinctive advantages when using PDX over cell lines for drug safety and efficacy studies as well as predicting patient tumor response to certain anti-cancer agents. Since PDX can be passaged without in vitro processing steps, PDX models allow the propagation and expansion of patient tumors without significant genetic transformation of tumor cells over multiple murine generations. Within PDX models, patient tumor samples grow in physiologically-relevant tumor microenvironments that mimic the oxygen, nutrient, and hormone levels that are found in the patient's primary tumor site. Furthermore, implanted tumor tissue maintains the genetic and epigenetic abnormalities found in the patient and the xenograft tissue can be excised from the patient to include the surrounding human stroma. As a result, numerous studies have found that PDX models exhibit similar responses to anti-cancer agents as seen in the actual patient who provided the tumor sample.

Computer Programs and Systems

The training data set and the classification models according to embodiments of the invention can be embodied by computer code that is executed or used by a digital computer. The computer code can be stored on any suitable computer readable media including optical or magnetic disks, sticks, tapes, transmission type media such as digital and analog, etc., and can be written in any suitable computer programming language including C, C++, Java, Python, etc.

The output data resulting from training can be displayed on any graphical display interface on a user device connectable to a digital computer or a server to which such a computer is connected (e.g., through the internet). Suitable digital computers include micro, mini, or large computers using any standard or specialized operating system such as a Unix, Windows™ or Linux™ based operating system. The digital computer that is used may be physically separate from the instrument used to obtain values for data elements in a profiling experiment. For example, the computer may be remote from a mass spectrometer that is used to create the spectra of interest, or it may be coupled to the mass spectrometer. The graphical interface also may be remote from the computer, for example, part of a wireless device connectable to the network.

The present disclosure also includes a computer system that has a database containing features of data elements/biomarkers characteristic of different cancers. In one aspect, the cell state comprises one or more of a stage of differentiation; the expression of a phenotype; a proliferation or stage of a cell cycle; a response to a stimulus, a disease, an agent (e.g., a toxin or a potentially toxic agent, a known or candidate drug; an antibiotic; an infectious or pathological organism; an environmental pollutant, etc.), a condition, and the like; environmental pollutant, a candidate drug, etc.) or condition (temperature, pH, etc.); and the like. In another aspect, the cell state reflects the status of the source of the cell. For example, the cell state may reflect a disease or other physiological response(s) or conditions being experienced by a patient from which the cell was derived (e.g., such as old age; a psychiatric condition; an addiction; an allergic reaction, etc.).

In one embodiment, the database comprises ranked or clustered biomarkers (i.e., biomarkers divided into subsets based on the discriminatory power of the biomarker). The biomarkers may be ranked or clustered according to association with various parameters. Such parameters include responses to toxins, disease, pollutants, conditions, stressors, developmental stage, drugs, therapeutic agents, antibiotics, and the like. The database comprises biomarkers which show a relatively narrow range of variability in a population for a given cell state but with high discrimination between cell states. For example, the biomarker is reproducibly associated with the parameter (greater than at least 80% specificity and greater than at least about 70% sensitivity in tests to detect or diagnose the parameter) and has a high discriminatory power.

However, it should be noted that discriminatory power is not the limiting characteristic of the biomarker. For example, for certain diseases with few or no satisfactory diagnostic tests, a biomarker with lower specificity and/or sensitivity would still have value.

The system additionally comprises a database management system. User requests or queries are formatted in an appropriate language understood by the database management system that processes the query to extract the relevant information from the database of training sets.

The system may additionally include records from an external database or may communicate with such an external database. Preferably, the system is connectable to a network to which a network server and one or more clients are connected. The Network may be a local area network (LAN) or a wide area network (WAN), as is known in the art. Preferably, the server includes the hardware necessary for running computer program products (e.g., software) to access database data for processing user requests. For example, one type of user request may be for the system to identify biomarkers associated with a selected cell state. Such as request may provide optional data options, e.g., such as sources of probes that might be used to detect one or more biomarkers (such as a link to a site providing binding partners for the biomarker(s), such as antibodies).

The system also includes an operating system (e.g., UNIX or Linux) for executing instructions from a database management system. In one aspect, the operating system also runs a World Wide Web application, and a World Wide Web server, thereby connecting the server to a network.

Preferably, the system includes one or more user devices that comprises a graphical display interface comprising interface elements such as buttons, pull down menus, scroll bars, fields for entering text, and the like as are routinely found in graphical user interfaces known in the art. Requests entered on a user interface are transmitted to an application program in the system (such as a Web application) for formatting to search for relevant information in one or more of the system databases. Requests or queries entered by a user may be constructed in any suitable database language (e.g., Sybase or Oracle SQL). In one embodiment, a user of user device in the system is able to directly access data using an HTML interface provided by Web browsers and Web server of the system.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

Non-Limiting Embodiments

Provided below are certain non-limiting Embodiments of different aspects of the present disclosure.

1. A method of using at least one hardware processor to train an artificial intelligence to identify one or more predictive biomarkers for cancer treatment, the method comprising: using at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and validating the prediction model by using a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model to further train the learning algorithm.

2. The method of Embodiment 1, wherein the human cancer tissue exhibiting the specific set of cancer biomarkers is orthotopically implanted into the multiple immune-deficient mice.

3. The method of Embodiment 1 or 2, wherein the at least one cancer drug discovery data set comprises cancer classification data, cancer biomarker data, drug or drug combination data, and biological response data.

4. The method of Embodiment 3, wherein for each cancer class, the at least one learning algorithm qualifies drugs or drug combinations in terms of their biological response.

5. The method of Embodiment 4, wherein for each drug or drug combination under the cancer class, the at least one learning algorithm qualifies cancer biomarkers in terms of their correspondence to the drug's or drug combination's biological response.

6. The method of any one of Embodiments 3-5, wherein the cancer classification data comprises cancer cell line information from in vitro screening, patient information from clinical studies, or combination thereof.

7. The method of Embodiment 6, wherein the cancer cell line information comprises information selected from the group consisting of cancer cell line identification, TCGA classification, tissue type, tissue sub-type, or combinations thereof.

8. The method of Embodiment 6, wherein the patient information comprises information selected from cancer type, patient age, patient gender, patient weight; patient family history, patient preexisting condition, and combinations thereof.

9. The method of any one of Embodiments 3-8, wherein the cancer biomarker data comprises gene expression data.

10. The method of Embodiment 9, wherein the gene expression data are normalized using transcripts per million (TPM).

11. The method of any one of Embodiments 9-10, wherein the gene expression data are normalized against the geometric mean of at least 4 housekeeping genes with low variance.

12. The method of any one of Embodiments 3-11, wherein the cancer biomarker data comprises gene methylation data.

13. The method of any one of Embodiments 3-12, wherein the cancer biomarker data comprises protein biomarker data.

14 The method of any one of Embodiments 3-13, wherein the drug or drug combination data comprises chemical structures of drugs.

15 The method of any one of Embodiments 3-14, wherein the drug or drug combination data comprises sub-structural features of drugs.

16. The method of Embodiment 15, wherein the sub-structural features of drugs comprise descriptors from SMILES specification of the drugs.

17. The method of any one of Embodiments 3-16, wherein the biological response data comprises in vitro drug screening results.

18. The method of Embodiment 17, wherein the in vitro drug screening results are in the form of IC50 (half maximal inhibitory concentration), AUC (area under the drug response curve), or combination thereof.

19. The method of any one of Embodiments 3-18, wherein the biological response data comprises in vitro drug combination screening results.

20. The method of Embodiment 19, wherein the in vitro drug combination screening results are in the form of synergy score obtained through a Highest single agent (HSA) model, Loewe additivity model, zero interaction potency (ZIP) model, or Bliss independence model.

21. The method of Embodiment 19, wherein the in vitro drug combination screening results are in the form of an AUC score.

22. The method of any one of Embodiments 3-21, wherein the biological response data comprises clinical study results.

23. The method of Embodiment 22, wherein the clinical study results comprise safety evaluation, efficacy evaluation, dose response evaluation, pharmacodynamic evaluation, pharmacokinetic evaluation, progression-free survival evaluation, or combinations thereof.

24. The method of Embodiment 23, wherein the efficacy evaluation comprises tumor size measurement, tumor burden evaluation, efficacy biomarker evaluation, or combinations thereof.

25. The method of any one of Embodiments 1-24, wherein the at least one cancer drug discovery data set comprise Genomics of Drug Sensitivity in Cancer (GDSC).

26. The method of any one of Embodiments 1-25, wherein the at least one cancer drug discovery data set comprise data from NCI Almanac or Drugcomb.org.

27. The method of any one of Embodiments 1-26, wherein the at least one cancer drug discovery data set comprise data from Cancer Genome Atlas Program.

28. The method of any one of Embodiments 1-27, wherein the at least one cancer drug discovery data set comprise data from Genotype Tissue Expression Project (GTEx).

29. The method of any one of Embodiments 1-28, wherein the at least one learning algorithm comprises a supervised learning algorithm.

30. The method of any one of Embodiments 1-28, wherein the at least one learning algorithm comprises an unsupervised learning algorithm.

31. The method of any one of Embodiments 1-30, wherein the at least one learning algorithm comprises a regression algorithm, preferably a random-forest regressor.

32. The method of any one of Embodiments 1-31, wherein the at least one learning algorithm comprises a classification algorithm, preferably a random-forest classifier, an SVM classifier, or both.

33. The method of any one of Embodiments 1-32, wherein the at least one learning algorithm comprises a feature selection algorithm, preferably a Boruta algorithm.

34. The method of any one of Embodiments 1-33, further comprising applying a dimension reduction algorithm, preferably UMAP, PCA, or both.

35. The method of any one of Embodiments 1-34, further comprising independently re-sampling data elements in each data set.

36. A system comprising: an input unit capable of downloading at least one cancer drug discovery data set; and training unit capable of using the at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and wherein the training unit is capable of further training the learning algorithm by using a xenograft mouse model, wherein, in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model.

37. The system of Embodiment 36, wherein the human cancer tissue exhibiting the specific set of cancer biomarkers is orthotopically implanted into the multiple immune-deficient mice.

38. The system of Embodiment 37, wherein the at least one cancer drug discovery data set comprises cancer classification data, cancer biomarker data, drug or drug combination data, and biological response data.

39. The system of Embodiment 38, wherein for each cancer type, the at least one learning algorithm qualifies drugs or drug combinations in terms of their biological response to the cancer type.

40. The system of Embodiment 39, wherein for each drug or drug combination under the cancer type, the at least one learning algorithm qualifies cancer biomarkers in terms of their correspondence to the drug's or drug combination's biological response to the cancer type.

41. The system of any one of Embodiments 38-40, wherein the cancer classification data comprises cancer cell line information from in vitro screening, patient information from clinical studies, or combination thereof.

42. The system of Embodiment 41, wherein the cancer cell line information from comprises information selected from the group consisting of cancer cell line identification, TCGA classification, tissue type, tissue sub-type, or combinations thereof.

43. The system of Embodiment 41, wherein the patient information comprises information selected from cancer type, patient age, patient gender, patient weight, patient family history, patient pre-existing condition, and combinations thereof.

44. The system of any one of Embodiments 38-43, wherein the cancer biomarker data comprises gene expression data.

45. The system of Embodiment 44, wherein the gene expression data are normalized using transcripts per million (TPM).

46. The system of any one of Embodiments 44-45, wherein the gene expression data are normalized against the geometric mean of 4 housekeeping genes with low variance.

47. The system of any one of Embodiments 38-46, wherein the cancer biomarker data comprises gene methylation data.

48. The system of any one of Embodiments 38-47, wherein the cancer biomarker data comprises proteomic biomarker data.

49. The system of any one of Embodiments 38-48, wherein the drug or drug combination data comprises chemical structures of drugs.

50. The system of any one of Embodiments 38-49, wherein the drug or drug combination data comprises substructural features of drugs.

51. The system of Embodiment 50, wherein the substructural features of drugs comprise descriptor from SMILES specification of the drugs.

52. The system of any one of Embodiments 38-51, wherein the biological response data comprises in vitro drug screening results.

53. The system of Embodiment 52, wherein the in vitro drug screening results are in the form of IC50 (half maximal inhibitory concentration), AUC (area under the drug response curve), or combination thereof.

54. The system of any one of Embodiments 38-53, wherein the biological response data comprises in vitro drug combination screening results.

55. The system of Embodiment 54, wherein the in vitro drug combination screening results are in the form of synergy score obtained through a Highest single agent (HSA) model, Loewe additivity model, zero interaction potency (ZIP) model, or Bliss independence model.

56. The system of Embodiment 54, wherein the in vitro drug combination screening results are in the form of an AUC score.

57. The system of any one of Embodiments 38-56, wherein the biological response data comprises clinical study results.

58. The system of Embodiment 57, wherein the clinical study results comprise safety evaluation, efficacy evaluation, dose response evaluation, pharmacodynamic evaluation, pharmacokinetic evaluation, progression-free survival evaluation, or combinations thereof.

59. The system of Embodiment 58, wherein the efficacy evaluation comprises tumor size measurement, tumor burden evaluation, efficacy biomarker evaluation, or combinations thereof.

60. The system of any one of Embodiments 36-59, wherein the at least one cancer drug discovery data set comprise Genomics of Drug Sensitivity in Cancer (GDSC).

61. The system of any one of Embodiments 36-60, wherein the at least one cancer drug discovery data set comprise data from NCI Almanac or Drugcomb.org.

62. The system of any one of Embodiments 36-61, wherein the at least one cancer drug discovery data set comprise data from Cancer Genome Atlas Program.

63. The system of any one of Embodiments 36-62, wherein the at least one cancer drug discovery data set comprise data from Genotype Tissue Expression Project (GTEx).

64. The system of any one of Embodiments 36-63, wherein the at least one learning algorithm comprises a supervised learning algorithm.

65. The system of any one of Embodiments 36-63, wherein the at least one learning algorithm comprises an unsupervised learning algorithm.

66. The system of any one of Embodiments 36-65, wherein the at least one learning algorithm comprises a regression algorithm, preferably a random-forest regressor.

67. The system of any one of Embodiments 36-66, wherein the at least one learning algorithm comprises a classification algorithm, preferably a random-forest classifier, an SVM classifier, or both.

68. The system of any one of Embodiments 36-67, wherein the at least one learning algorithm comprises a feature selection algorithm, preferably a Boruta algorithm.

69. The system of any one of Embodiments 36-68, further comprising a dimension reduction algorithm, preferably UMAP, PCA, or both.

70. The system of any one of Embodiments 36-69, wherein the system is capable of independently re-sampling data elements in each data set.

71. A non-transitory computer-readable medium having instructions stored therein, wherein the instructions, when executed by a processor, cause the processor to use at least one cancer drug discovery data set to train at least one learning algorithm in a prediction model, wherein the trained prediction model is capable of qualifying a plurality of drugs or drug combinations in terms of their predicted biological response to a human cancer tissue exhibiting a specific set of cancer biomarkers; and train the prediction model by using a xenograft mouse model, wherein in the xenograft mouse model, the human cancer tissue exhibiting the specific set of cancer biomarkers is implanted in parallel into multiple immune-deficient mice each subsequently treated in parallel with one of the plurality of drugs or drug combinations, with biological response of the treatment fed back to the prediction model to further train the learning algorithm.

72. The non-transitory computer-readable medium of Embodiment 71, wherein the human cancer tissue exhibiting the specific set of cancer biomarkers is orthotopically implanted into the multiple immune-deficient mice.

73. The non-transitory computer-readable medium of Embodiment 72, wherein the at least one cancer drug discovery data set comprises cancer classification data, cancer biomarker data, drug or drug combination data, and biological response data.

74. The non-transitory computer-readable medium of Embodiment 73, wherein for each cancer type, the at least one learning algorithm qualifies drugs or drug combinations in terms of their biological response to the cancer type.

75. The non-transitory computer-readable medium of Embodiment 74, wherein for each drug or drug combination under the cancer type, the at least one learning algorithm qualifies cancer biomarkers in terms of their correspondence to the drug's or drug combination's biological response to the cancer type 76. The non-transitory computer-readable medium of any one of Embodiments 73-75, wherein the cancer classification data comprises cancer cell line information from in vitro screening, patient information from clinical studies, or combination thereof.

77. The non-transitory computer-readable medium of Embodiment 76, wherein the cancer cell line information from comprises information selected from the group consisting of cancer cell line identification, TCGA classification, tissue type, tissue sub-type, or combinations thereof.

78. The non-transitory computer-readable medium of Embodiment 76, wherein the patient information comprises information selected from cancer type, patient age, patient gender, patient weight; patient family history, patient pre-existing condition, and combinations thereof.

79. The non-transitory computer-readable medium of any one of Embodiments 73-78, wherein the cancer biomarker data comprises gene expression data.

80. The non-transitory computer-readable medium of Embodiment 79, wherein the gene expression data are normalized using transcripts per million (TPM).

81. The non-transitory computer-readable medium of any one of Embodiments 79-80, wherein the gene expression data are normalized against the geometric mean of 4 housekeeping genes with low variance.

82. The non-transitory computer-readable medium of any one of Embodiments 73-81, wherein the cancer biomarker data comprises gene methylation data.

83. The non-transitory computer-readable medium of any one of Embodiments 73-82, wherein the cancer biomarker data comprises protein biomarker data.

84. The non-transitory computer-readable medium of any one of Embodiments 73-83, wherein the drug or drug combination data comprises chemical structures of drugs.

85. The non-transitory computer-readable medium of any one of Embodiments 73-84, wherein the drug or drug combination data comprises sub-structural features of drugs.

86. The non-transitory computer-readable medium of Embodiment 85, wherein the sub-structural features of drugs comprise descriptor from SMILES specification of the drugs.

87. The non-transitory computer-readable medium of any one of Embodiments 73-86, wherein the biological response data comprises in vitro drug screening results.

88. The non-transitory computer-readable medium of Embodiment 87, wherein in vitro drug screening results are in the form of IC50 (half maximal inhibitory concentration), AUC (area under the drug response curve), or combination thereof.

89. The non-transitory computer-readable medium of any one of Embodiments 73-88, wherein the biological response data comprises in vitro drug combination screening results.

90. The non-transitory computer-readable medium of Embodiment 89, wherein in vitro drug combination screening results are in the form of synergy score obtained through a Highest single agent (HSA) model, Loewe additivity model, zero interaction potency (ZIP) model, or Bliss independence model.

91. The non-transitory computer-readable medium of Embodiment 89, wherein in vitro drug combination screening results are in the form of an AUC score.

92. The non-transitory computer-readable medium of any one of Embodiments 73-91, wherein the biological response data comprises clinical study results.

93. The non-transitory computer-readable medium of Embodiment 92, wherein the clinical study results comprise safety evaluation, efficacy evaluation, dose response evaluation, pharmacodynamic evaluation, pharmacokinetic evaluation, progression-free survival evaluation, or combinations thereof.

94. The non-transitory computer-readable medium of Embodiment 93, wherein the efficacy evaluation comprises tumor size measurement, tumor burden evaluation, efficacy biomarker evaluation, or combinations thereof.

95. The non-transitory computer-readable medium of any one of Embodiments 71-94, wherein the at least one cancer drug discovery data set comprise Genomics of Drug Sensitivity in Cancer (GDSC).

96. The non-transitory computer-readable medium of any one of Embodiments 71-95, wherein the at least one cancer drug discovery data set comprise data from NCI Almanac or Drugcomb.org.

97. The non-transitory computer-readable medium of any one of Embodiments 71-96, wherein the at least one cancer drug discovery data set comprise data from Cancer Genome Atlas Program.

98. The non-transitory computer-readable medium of any one of Embodiments 71-97, wherein the at least one cancer drug discovery data set comprise data from Genotype Tissue Expression Project (GTEx).

99. The non-transitory computer-readable medium of any one of Embodiments 71-98, wherein the at least one learning algorithm comprises a supervised learning algorithm.

100. The non-transitory computer-readable medium of any one of Embodiments 71-98, wherein the at least one learning algorithm comprises an unsupervised learning algorithm.

101. The non-transitory computer-readable medium of any one of Embodiments 71-100, wherein the at least one learning algorithm comprises a regression algorithm, preferably a random-forest regressor.

102. The non-transitory computer-readable medium of any one of Embodiments 71-101, further comprising dimension reduction algorithms of data elements in each data set, preferably UMAP, PCA, or both.

103. The non-transitory computer-readable medium of any one of Embodiments 71-102, wherein the at least one learning algorithm comprises a classification algorithm, preferably a random-forest classifier, an SVM classifier, or both.

104. The non-transitory computer-readable medium of any one of Embodiments 71-103, wherein the at least one learning algorithm comprises a feature selection algorithm, preferably a Boruta algorithm.

105. The non-transitory computer-readable medium of any one of Embodiments 71-104, wherein the non-transitory computer-readable medium is capable of independently re-sampling data elements in each data set.

Non-Limiting Examples

Provided below are certain non-limiting examples according to different aspects of the present disclosure. To examine how different aspects of the present disclosure affect the resulting prediction accuracy, a range of models were built for monotherapy predictions (FIG XA) as well as combined therapies that include both monotherapies and combination therapy predictions (FIG XB).

Genomics of Drug Sensitivity in Cancer (GDSC).
Drugcomb.org.
National Cancer Institute ALMANAC.
Cancer Genome Atlas Program.
Genotype Tissue Expression Project (GTEx).

A broad spectrum of machine learning methods has been applied to the drug response prediction problem: regularized regression methods (e.g. lasso, elastic net, ridge regression), partial least squares (PLS) regression, support vector machines (SVM), random forest (RF), neural networks and deep learning, logical models, or kernelized bayesian matrix factorization (KBMF). However, no systematic exploration of model training strategies based on data from multiple large cell line screens has been reported so far. Also, cell line-based models have not yet been compared to xenograft-based models. The current study closes these gaps with the ultimate goal of improving accuracy of drug response prediction in cell lines and xenografts.

At the outset, the influence of different modelling parameters (e.g. response metric, number of features, type of features) on predictive performance in drug sensitivity testing was systematically study. Four drugs (doxorubicin, gemcitabine, olaparib, and palbociclib) were used in this non-limiting example, in which drug sensitivity for all of the four drugs is available in each data set. Predictive performance was assessed by xenograft mouse model validation. The best parameter set and strategy from this analysis was selected and checked whether drug sensitivity in animal xenograft systems could be predicted by training of models from cell line-based and clinical based data. Since in xenograft experiments each drug was tested on samples from a particular tissue type, the cancer discover data sets were restricted accordingly, e.g. for drug response prediction all cell line-based and clinical study-based data used for this modelling task were from the same cancer classification as the xenograft sample. The process of this non-limiting example is illustrated in FIG. 1.

Predictive Model

Classes of Supervised Learning

Figure 2:
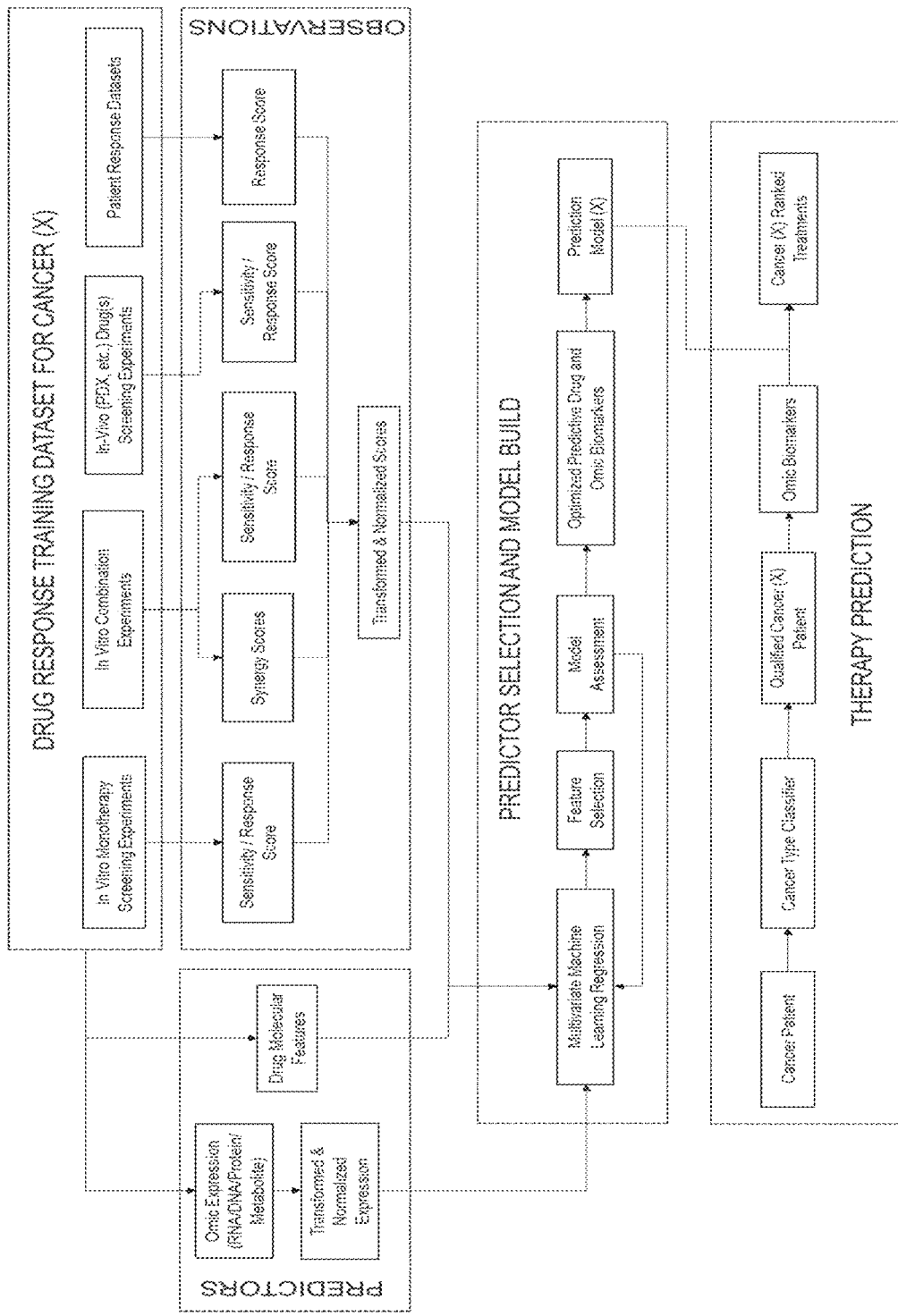
FIG. 2 is a schematic diagram detailing the algorithm used for the creation of software to identify molecular chemical predictors and predictive gene biomarkers for cancer treatment. Training data from each cancer type (X) is processed separately to build a machine learning model to predict treatment for each cancer type.

Drug response prediction tasks and division rate/slope of growth curve prediction were regression tasks (FIG. 2). Tissue type prediction tasks to qualify which cancer AI model to use were classification tasks. Additionally, some early drug response prediction tasks against TCGA clinical datasets were classification tasks.

Modelling Methods and Hyperparameters

For regression tasks, our best performing modelling method was random forest. For classification tasks, our top performing modelling method was also random forest. Each modelling method has its own set of hyperparameters. For random forest regression, the most important hyperparameters include the maximum depth of the individual trees (max_depth), the number of trees in the forest (n_estimators), and the criteria with which to split on (criterion).

Feature Selection

In order to select a subset of all available features for modelling, feature selection using only data from the training set was performed. For the drug response prediction tasks, a multi-step feature selection process is used to fine tune our model (FIG. 2). At first, the top 1000 drug molecular features predictive of drug response in each cancer type were selected. In random forest, "IncNodePurity" or variable importance values are sorted and the top 1000 are initially chosen. Next, the Boruta algorithm is used to further refine the drug molecular feature selection to a smaller subset producing optimal accuracy to the model. Approximately 20,000 gene expression features (HK-ratio) are added to the refined drug molecular features (~30-40) and trained against drug response to find the top 1000 gene features. Again, Boruta is used to reduce the genes down to only a handful of significant genes (30-40). Gene biomarker optimization is performed to further reduce the total number of genes to 5-10 genes (FIG. 3). The molecular features and optimized gene biomarkers are now used for predicting therapy on the cancer type subset used in the initial training. This task is performed on every cancer type subset with available training data.

Results

Performance Evaluation of Prediction Models

Bagging, or bootstrap aggregation were utilized to create multiple datasets and evaluate the model's performance on each of them for performance validation of the random forest regression model. The results of the random forest regression prediction on in-vitro datasets for monotherapy drugs utilizing growth curve endpoints (AUC) show that the model performs well with an average $R^2$ 0.651, RMSE of 0.094, and accuracy of 90% (FIG. 4A). Both monotherapies and combination therapies were then evaluated together by converting AUC scores from the monotherapies and synergy scores from the combinations to normalized Z-Scores. When combined, the model's average $R^2$ was 0.569, RMSE of 0.686, and accuracy of 83% (FIG. 4B).

Figure 5:
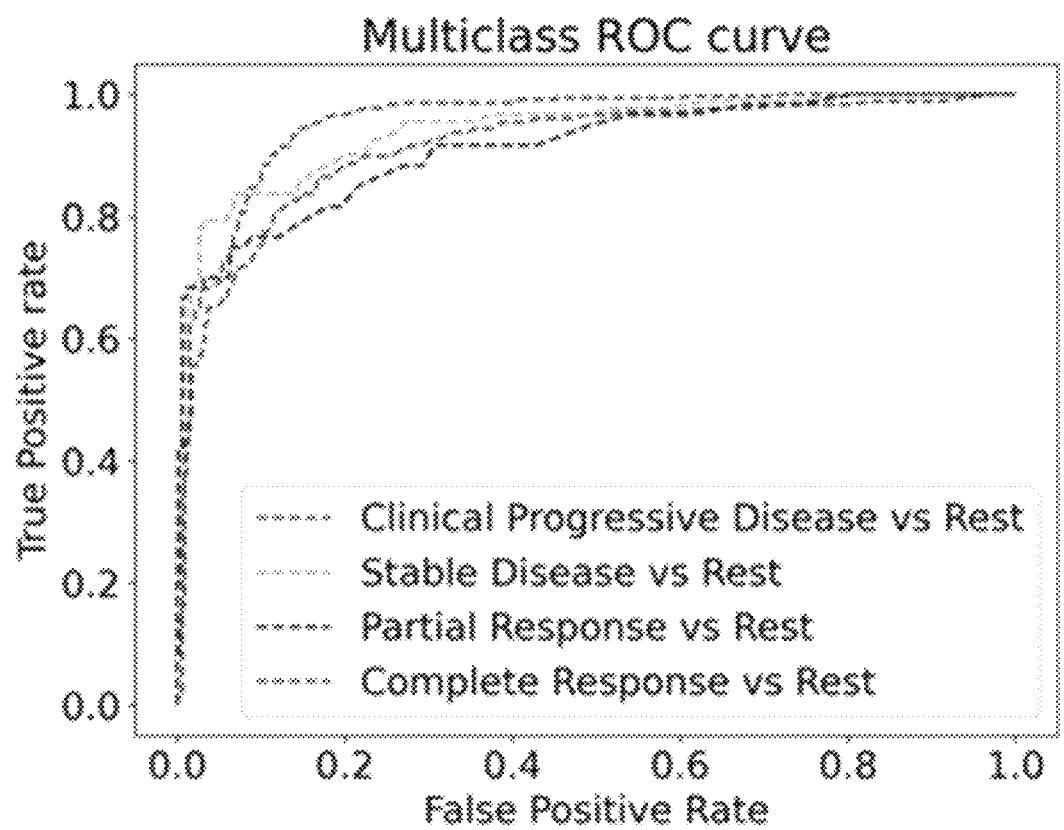
FIG. 5 demonstrates results from our machine learning model for clinical therapy response in cancer patients.

For TCGA clinical response evaluation, random forest classification to model therapy response in patients were performed. The entire clinical response dataset from TCGA were combined for this evaluation due to the smaller dataset size (2212 total). RECIST criteria classes were used to construct a four-class response variable that categorized patients into the following classifications following various therapy treatments: complete response (CR), partial response (PR), stable disease (SD), and progressive disease (PD). Receiver operating characteristic (ROC) area under the curve (AUC) demonstrated good model accuracy for predicting the correct response class, with an average of ROC AUC of 0.93 (FIG. 5).

Xenograft Validation

Gene expression was measured as continuous TPM (transcripts per million mapped reads) values from RNA-seq. TPM values are normalized to a set of house-keeping genes (HK-ratio). The HK-ratio of each gene biomarker from the PDX is supplied to the appropriate cancer type prediction model to determine a ranked list of therapy treatments (FIG. 2). Top ranked therapies are tested in the PDX to validate the accuracy of therapy predictions. In one such example, 4 AI predicted therapies on a triple negative breast cancer orthotopic PDX model were tested. The results demonstrated complete tumor growth inhibition for the top AI predicted monotherapy (FIG. 6).

What is claimed is:

1. A method of using at least one hardware processor to train at least one machine learning algorithm being in a prediction model for drug response of a plurality of drugs to a cancer in a human patient diagnosed with the cancer, the method comprising:
   using at least one cancer drug discovery data set comprising sub-structural features of the plurality of drugs comprising a descriptor from SMILES specification of the plurality of drugs, cancer biomarker data comprising gene expression data, and externally sourced drug response training dataset associated with the plurality of drugs and the cancer, to train the at least one machine learning algorithm in the prediction model,
   using the prediction model to qualify a subset of drugs or drug combinations from the plurality of drugs in terms of their predicted biological response to a cancerous tissue of the human patient exhibiting gene expressions of a set of cancer biomarkers, wherein the cancerous tissue of the human patient is in the form of tumor fragments and not cancer cell lines;
   implanting, in parallel, the cancerous tissue of the human patient exhibiting the gene expressions of the set of cancer biomarkers into multiple immune-deficient mice each subsequently administered a treatment with one of the subset of drugs or drug combinations; and
   validating the prediction model by feeding back data corresponding to biological response of the treatment from the multiple immune-deficient mice, to the prediction model to further train the machine learning algorithm.

2. The method of claim 1, wherein the human tissue of the cancer exhibiting the set of cancer biomarkers is orthotopically implanted into the multiple immune-deficient mice.

3. The method of claim 1, wherein the at least one cancer drug discovery data set comprises cancer classification data, cancer biomarker data, drug or drug combination data, and biological response data.

4. The method of claim 3, wherein for each cancer class, the at least one machine learning algorithm qualifies drugs or drug combinations in terms of their biological response.

5. The method of claim 4, wherein for each drug or drug combination under the cancer class, the at least one machine learning algorithm qualifies cancer biomarkers in terms of their correspondence to the drug's or drug combination's biological response.

6. The method of claim 3, wherein the cancer classification data comprises cancer cell line information from in vitro screening, patient information from clinical studies, or combination thereof.

7. The method of claim 6, wherein the cancer cell line information comprises information selected from the group consisting of cancer cell line identification, TCGA classification, tissue type, tissue sub-type, or combinations thereof.

8. The method of claim 6, wherein the patient information comprises information selected from cancer type, patient age, patient gender, patient weight; patient family history, patient preexisting condition, and combinations thereof.

9. The method of claim 1, wherein the gene expression data are normalized using transcripts per million (TPM).

10. The method of claim 1, wherein the gene expression data are normalized against the geometric mean of at least 4 housekeeping genes with low variance.

11. The method of claim 3, wherein the cancer biomarker data comprises gene methylation data.

12. The method of claim 3, wherein the cancer biomarker data comprises protein biomarker data.

13. The method of claim 3, wherein the drug or drug combination data comprises chemical structures of drugs.

14. The method of claim 13, wherein the drug or drug combination data comprises sub-structural features of drugs.

15. The method of claim 14, wherein the sub-structural features of drugs comprise descriptors from SMILES specification of the drugs.

16. The method of claim 3, wherein the biological response data comprises in vitro drug screening results.

17. The method of claim 16, wherein the in vitro drug screening results are in the form of IC50 (half maximal inhibitory concentration), AUC (area under the drug response curve), or combination thereof.

18. The method of claim 3, wherein the biological response data comprises in vitro drug combination screening results.

19. The method of claim 18, wherein the in vitro drug combination screening results are in the form of synergy score obtained through a Highest single agent (HSA) model, Loewe additivity model, zero interaction potency (ZIP) model, or Bliss independence model.

20. The method of claim 18, wherein the in vitro drug combination screening results are in the form of an AUC score.

21. The method of claim 3, wherein the biological response data comprises clinical study results.

22. The method of claim 21, wherein the clinical study results comprise safety evaluation, efficacy evaluation, dose response evaluation, pharmacodynamic evaluation, pharmacokinetic evaluation, progression-free survival evaluation, or combinations thereof.

23. The method of claim 22, wherein the efficacy evaluation comprises tumor size measurement, tumor burden evaluation, efficacy biomarker evaluation, or combinations thereof.

24. The method of claim 1, wherein the at least one cancer drug discovery data set comprise Genomics of Drug Sensitivity in Cancer (GDSC), data from NCI Almanac or Drugcomb.org, data from Cancer Genome Atlas Program, data from Genotype Tissue Expression Project (GTEx), or combinations thereof.

25. The method of claim 1, wherein the at least one machine learning algorithm comprises a regression algorithm, and optionally wherein the regression algorithm comprises a random-forest regressor.

26. The method of claim 1, wherein the at least one machine learning algorithm comprises a classification algorithm, and optionally wherein the classification algorithm comprises a random-forest classifier, an SVM classifier, or both.

27. The method of claim 1, wherein the at least one machine learning algorithm comprises a feature selection algorithm, and optionally wherein the feature selection algorithm comprises a Boruta algorithm.

28. The method of claim 1, further comprising applying a dimension reduction algorithm, and optionally wherein the dimension reduction algorithm comprises UMAP, PCA, or both.

29. The method of claim 1, further comprising independently re-sampling data elements in each data set.

30. A method of using at least one hardware processor to train at least one machine learning algorithm being in a prediction model for drug response of a plurality of drugs to a cancer in a human patient diagnosed with the cancer, the method comprising:

using at least one cancer drug discovery data set comprising sub-structural features of the plurality of drugs comprising a descriptor from SMILES specification of the plurality of drugs, cancer biomarker data comprising gene expression data, and externally sourced drug response training dataset associated with the plurality of drugs and the cancer, the drug response training dataset comprising data associated with in vitro monotherapy drug screening data sets, in vitro cell line combination data sets, in vivo drugs screening experiments of the plurality of drugs, and clinical study data set, to train the at least one machine learning algorithm comprising a feature selection algorithm to refine the sub-structural features of the plurality of drugs to a smaller subset of drug molecular features and the gene expression data to a smaller subset of gene expression data in the prediction model, using the prediction model after training the at least one machine learning algorithm, qualifying a subset of drugs or drug combinations from the plurality of drugs in terms of their predicted biological response to a cancerous tissue of the human patient exhibiting gene expressions of a set of cancer biomarkers, wherein the cancerous tissue of the human patient is in the form of tumor fragments and not cancer cell lines;

implanting, in parallel, the cancerous tissue of the human patient exhibiting the gene expressions of the set of cancer biomarkers into multiple immune-deficient mice each subsequently administered a treatment with one of the subset of drugs or drug combinations; and validating the prediction model by feeding back data corresponding to biological response of the treatment from the multiple immune-deficient mice, to the prediction model to further train the machine learning algorithm.

* * * * *